(12) United States Patent
Gibson et al.

(10) Patent No.: US 11,408,020 B2
(45) Date of Patent: *Aug. 9, 2022

(54) METHODS FOR IN VITRO JOINING AND COMBINATORIAL ASSEMBLY OF NUCLEIC ACID MOLECULES

(71) Applicant: CODEX DNA, INC., San Diego, CA (US)

(72) Inventors: Daniel G. Gibson, Crofton, MD (US); Hamilton O. Smith, San Diego, CA (US); Clyde A. Hutchison, La Jolla, CA (US); Lei Young, Gaithersburg, MD (US); J. Craig Venter, La Jolla, CA (US)

(73) Assignee: Codex DNA, Inc., San Diego, CA (US)

( * ) Notice: Subject to any disclaimer, the term of this patent is extended or adjusted under 35 U.S.C. 154(b) by 475 days.

This patent is subject to a terminal disclaimer.

(21) Appl. No.: 16/388,722

(22) Filed: Apr. 18, 2019

(65) Prior Publication Data

US 2019/0241921 A1    Aug. 8, 2019

Related U.S. Application Data

(60) Continuation of application No. 14/636,082, filed on Mar. 2, 2015, now Pat. No. 10,266,865, which is a
(Continued)

(51) Int. Cl.
*C12Q 1/68* (2018.01)
*C12P 19/34* (2006.01)
(Continued)

(52) U.S. Cl.
CPC .............. *C12P 19/34* (2013.01); *C12N 9/22* (2013.01); *C12N 9/93* (2013.01); *C12N 15/10* (2013.01);
(Continued)

(58) Field of Classification Search
CPC ........................................................ C12Q 1/68
(Continued)

(56) References Cited

U.S. PATENT DOCUMENTS 6,183,960 B1 * 2/2001 Lizardi ............... C12Q 1/6858
435/6.12
6,379,964 B1    4/2002 Del Cardayre et al.
(Continued)

FOREIGN PATENT DOCUMENTS

WO    WO 98/38297 A1    9/1998
WO    WO 2007/029144 A2    2/2007
WO    WO 2007/032837 A2    3/2007

OTHER PUBLICATIONS

Coco et al.: "*DNA Shuffling Method for Generating Highly Recombined Genes and Evolved Enzymes*,"; Nature Biotechnol. (2001), 19:354-359, Nature Publishing Group.
(Continued)

*Primary Examiner* — Aaron A Priest
(74) *Attorney, Agent, or Firm* — DLA Piper LLP (US)

(57) ABSTRACT

The present invention relates to methods of joining two or more double-stranded (ds) or single-stranded (ss) DNA molecules of interest in vitro, wherein the distal region of the first DNA molecule and the proximal region of the second DNA molecule of each pair share a region of sequence identity. The method allows the joining of a large number of DNA fragments, in a predetermined order and orientation, without the use of restriction enzymes. It can be used, e.g., to join synthetically produced sub-fragments of a gene or genome of interest. Kits for performing the method are also disclosed. The methods of joining DNA molecules may be used to generate combinatorial libraries useful to generate,
(Continued)

for example, optimal protein expression through codon optimization, gene optimization, and pathway optimization.

17 Claims, 14 Drawing Sheets

Specification includes a Sequence Listing.

Related U.S. Application Data division of application No. 12/371,543, filed on Feb. 13, 2009, now Pat. No. 8,968,999.

(60) Provisional application No. 61/142,101, filed on Dec. 31, 2008, provisional application No. 61/098,202, filed on Sep. 18, 2008, provisional application No. 61/052,614, filed on May 12, 2008, provisional application No. 61/064,107, filed on Feb. 15, 2008, provisional application No. 61/029,312, filed on Feb. 15, 2008.

(51) Int. Cl.
| | |
|---|---|
| *C12N 15/10* | (2006.01) |
| *C12N 15/64* | (2006.01) |
| *C12N 9/22* | (2006.01) |
| *C12N 9/00* | (2006.01) |
| *C12N 15/66* | (2006.01) |

(52) U.S. Cl.
CPC ......... *C12N 15/1027* (2013.01); *C12N 15/64* (2013.01); *C12N 15/66* (2013.01)

(58) Field of Classification Search
USPC .......................................................... 435/6
See application file for complete search history.

(56) References Cited

U.S. PATENT DOCUMENTS

| | | |
|---|---|---|
| 6,458,544 B1 | 10/2002 | Miller |
| 6,821,758 B1 | 11/2004 | Koltermann et al. |
| 7,723,077 B2 | 5/2010 | Young et al. |
| 2004/0191871 A1* | 9/2004 | Hyman .................. C12N 15/64 |
| | | 435/320.1 |
| 2005/0202490 A1* | 9/2005 | Makarov .............. C12Q 1/6827 |
| | | 435/6.12 |
| 2007/0037197 A1 | 2/2007 | Young et al. |
| 2010/0071085 A1* | 3/2010 | Lindbo .............. C12N 15/8203 |
| | | 800/278 |

OTHER PUBLICATIONS

Coljee et al.: "*Seamless Gene Engineering Using RNA- and DNA-Overhang Cloning,*"; Nature Biotechnol. (2000), 18:789-791, Nature America Inc.

Extended European Search Report dated Jul. 18, 2016, regarding EP 16165528.7.

European Patent Office Communication dated Aug. 19, 2013, regarding EP 09711127.2.

Gibson et al.: "*Complete Chemical Synthesis, Assembly, and Cloning of a Mycoplasma genitalium Genome,*"; Science (2008), 319(5867). 1215-1220, Blackwell Science Ltd.

Gibson et al.: "*Enzymatic Assembly of DNA Molecules up to Several Hundred Kilobases,*"; Nature Methods (2009), 6(5):343-345 + Methods, Nature America, Inc.

Moretti, Tamyra et al.: "*Enhancement of PCR Amplification Yield and Specificity Using AmpliTaq GoldTM DNA Polymerase*"; BioTechniques 25:716-722 (Oct. 1998).

Walker et al.: "*Isothermal in vitro Amplification of DNA by a Restriction Enzyme/DNA Polymerase System,*"; Proc. Natl. Acad. Sci. USA(1992) 89:392-396.

* cited by examiner

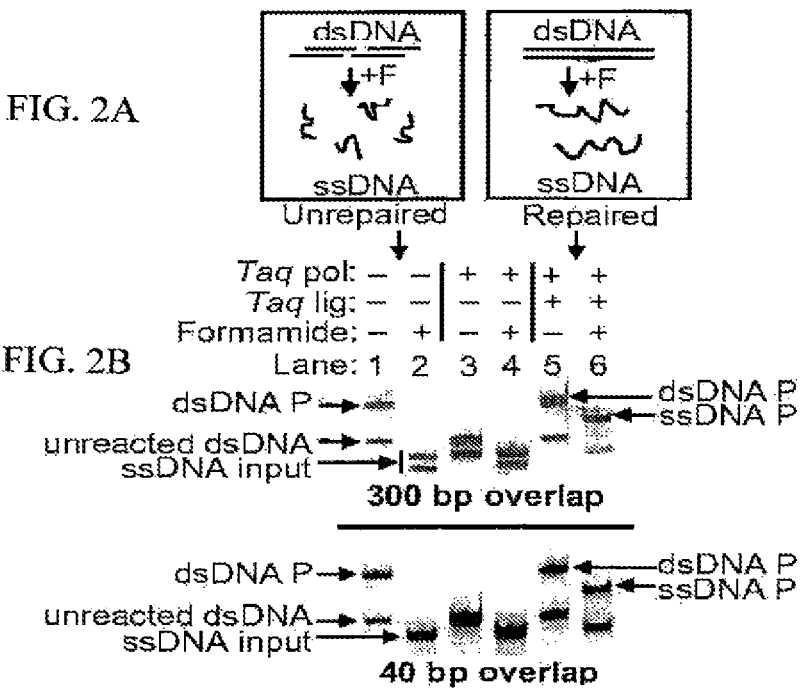
FIG. 2A
FIG. 2B
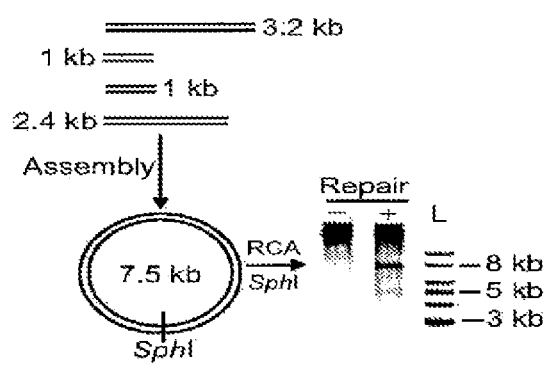
FIG. 3

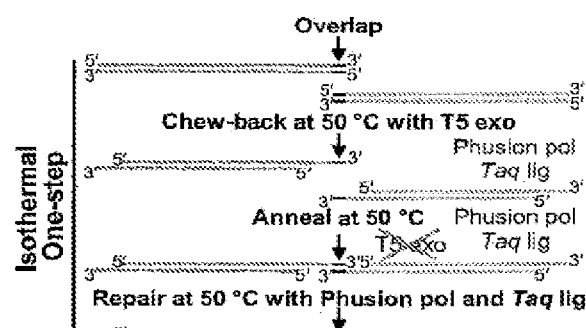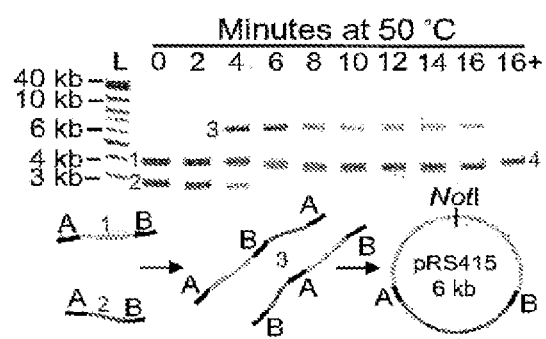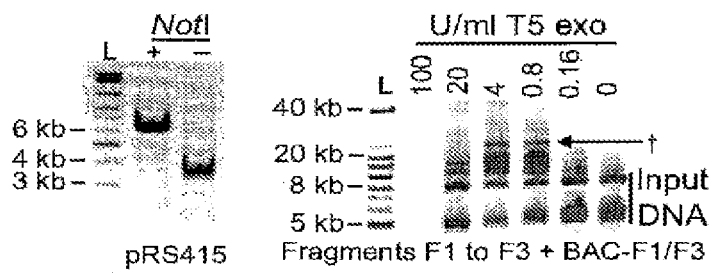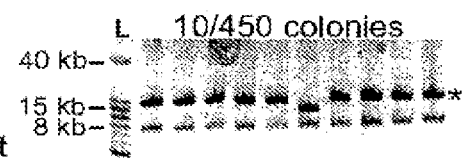
FIG. 5A
FIG. 5B
FIG. 5C
FIG. 5D
FIG. 5E

METHODS FOR IN VITRO JOINING AND COMBINATORIAL ASSEMBLY OF NUCLEIC ACID MOLECULES

CROSS-REFERENCE TO RELATED APPLICATIONS

This application is a continuation application of U.S. application Ser. No. 14/636,082 filed Mar. 2, 2015, now issued as U.S. Pat. No. 10,266,865; which is a divisional application of U.S. application Ser. No. 12/371,543 filed Feb. 13, 2009, now issued as U.S. Pat. No. 8,968,999; which claims the benefit under 35 USC § 119(e) to U.S. Application Ser. No. 61/142,101 filed Dec. 31, 2008, U.S. Application Ser. No. 61/098,202 filed Sep. 18, 2008, U.S. Application Ser. No. 61/052,614 filed May 12, 2008, U.S. Application Ser. No. 61/064,107 filed Feb. 15, 2008 and U.S. Application Ser. No. 61/029,312 filed Feb. 15, 2008. The disclosure of each of the prior applications is considered part of and is incorporated by reference in the disclosure of this application.

BACKGROUND OF THE INVENTION

Field of the Invention

The invention concerns methods for in vitro joining of single-stranded and/or double-stranded nucleic acid molecules permitting efficient one-step assembly of multiple nucleic acid molecules with overlapping terminal sequences. Invention methods are particularly useful in effecting systematic combinatorial assembly of fragments of nucleic acid sequence variants to modify properties of the joined nucleic acid sequence, for example, nucleic acid sequences providing variants of codon usage, control sequences, genes, pathways, chromosomes, extra-chromosomal nucleic acids, and genomes.

Background Information

A two-step thermocycler-based method was used to assemble portions of the *M. genitalium* genome, as described in Gibson, D. G., et al., "Complete chemical synthesis, assembly, and cloning of a *Mycoplasma genitalium* genome." *Science* (2008) 319:1215-1220. Another approach is described by Li, M. Z., et al., *Nature Meth.* (2007) 4:251-256. A single-step method of assembly employing T7 5' exonuclease and single-stranded DNA binding protein is disclosed in PCT publication WO2006/021944. The present invention discloses one-step procedures which facilitate assembly of DNA molecules in vitro. These methods employ either a non-thermostable 5' exonuclease that lacks 3' exonuclease activity or a 3' exonuclease that is functional in the presence of dNTPs.

These new methods are particularly useful in an additional aspect of the invention which provides systematic combinatorial assembly to modify nucleic acid molecules. Combinatorial techniques for assembly of chemical compounds for use in high throughput screening is by now well established. In addition, gene shuffling techniques in which coding sequences are randomly fragmented and reannealed have been practiced for a number of years. For instance, protocols to create libraries of chimeric gene fragments are described in Meyer, M., et al, "Combinatorial Recombination of Gene Fragments to Construct a Library of Chimeras" *Current Protocols in Protein Science* (2006) 26.2.1-26.2.17; McKee, A. E., et al., *JBEI* abstract. There is, however, a need for a systematic approach to combinatorial approach that does not rely on random rearrangement or shuffling to provide optimized nucleic acid sequences, for example, with optimized coding sequences or metabolic pathways, that can be selected according to desired properties. The present invention fills this need by providing a systematic combinatorial approach to assemble a variety of nucleic acids of interest.

Techniques for assembling various components into complete or minimal genomes have been established. For example, U.S. Patent Publication 2000/0264688, published 15 Nov. 2007, describes methods for constructing a synthetic genome by generating and assembling cassettes comprising portions of the genome. A stepwise hierarchical method to assemble nucleic acids is described in U.S. Patent Publication 2007/004041, published 4 Jan. 2007. However, no suggestion is made of using these techniques systematically to assemble a desired nucleic acid molecule.

It is understood that construction of a genome need not include all of the components that occur naturally. PCT Publication WO2007/047148 describes a minimal genome based on *Mycoplasma genitalium* wherein as many as 101 genes encoding proteins can be omitted and still retain viability. There is no suggestion that the components of the minimal genome be systematically assembled as combinatorial libraries permitting the formation of a multiplicity of alternative minimal genomes.

The present invention, thus, is directed to systematic methods and the products thereof that permit efficient and extensive modification of nucleic acid molecules to provide and screen nucleic acid assemblies of interest in a high-throughput manner, and readily adaptable to robotic implementation. In alternative embodiments, assembly reactions can be performed on a solid surface as opposed to in a reaction tube, for example, on a chip using microfluidics (such as shown in Huang, Y., et al., *Lab Chip* (2007) 7:24-26).

The techniques for systematic combinatorial assembly of nucleic acids representing variant coding sequences, expression systems, pathway synthesis and minimal or larger genomes employ in vitro assembly techniques at least in part. Any suitable in vitro assembly technique may be employed; however, the methods of the present invention include improvements on those already described in the art.

SUMMARY OF THE INVENTION

In a first aspect, the invention provides an in vitro method of joining a set of two or more double-stranded (ds) or single-stranded (ss) DNA molecules. The adjacent DNA molecules to be joined contain overlapping sequences at their termini. The two or more DNA molecules are contacted in vitro in a single vessel with (a) an isolated non-thermostable 5' to 3' exonuclease that lacks 3' exonuclease activity, (b) a crowding agent, (c) an isolated thermostable non-strand-displacing DNA polymerase with 3' exonuclease activity, or a mixture of said DNA polymerase with a second DNA polymerase that lacks 3' exonuclease activity, (d) an isolated thermostable ligase, (e) a mixture of dNTPs, and (f) a suitable buffer, under conditions that are effective for joining the two or more DNA molecules to form a first assembled dsDNA molecule in a one-step reaction.

In some embodiments, the exonuclease of (a) is a T5 exonuclease and the contacting is under isothermal conditions, and/or the crowding agent of (b) is PEG, and/or the non-strand-displacing DNA polymerase of (c) is PHU- SION® DNA polymerase or VENT$_R$® DNA polymerase, and/or the ligase of (d) is Taq ligase.

In some embodiments, the conditions are also suitable for digesting any unpaired, non-homologous, single-stranded DNAs following the joining reaction. At least some of the DNA molecules to be joined comprise, at one terminus, a sequence that is non-homologous to any of the DNA molecules of interest. Optionally, the non-homologous sequences comprise one or more binding regions for PCR primers, and/or regions of homology to vector sequences, and/or recognition sites for one or more restriction enzymes that are not present within the DNA molecules of interest, e.g., rare-cutting restriction enzymes.

The method may be employed to join a second set of two or more DNA molecules to one another to obtain a second assembled DNA molecule in addition to a first assembled molecule, and the first and the second assembled DNA molecules joined to obtain a third assembled ds DNA molecule. This process may be sequentially repeated as required to obtain the whole nucleic acid sequence of interest.

The invention also provides kits for performing the above methods that comprise: (a) an isolated non-thermostable 5' to 3' exonuclease that lacks 3' exonuclease activity, (b) a crowding agent, (c) an isolated thermostable non-strand-displacing DNA polymerase with 3' exonuclease activity, or a mixture of said DNA polymerase with a second DNA polymerase that lacks 3' exonuclease activity, and (d) an isolated thermostable ligase, in appropriate amounts. For example, the kit may contain T5 exonuclease, PEG, PHUSION® DNA polymerase, and Taq ligase.

In a second aspect, the invention is directed to an alternative in vitro method of joining a set of two or more double-stranded (ds) or single-stranded (ss) DNA molecules, where adjacent DNA molecules to be joined contain overlapping sequences at their termini. The method comprises contacting in vitro the two or more DNA molecules in a single vessel with (a) an isolated non-thermos table 3' to 5' exonuclease active in the presence of dNTPs, (b) a crowding agent, (c) an isolated heat-activated DNA polymerase, (d) an isolated thermostable ligase, (e) a mixture of dNTPs, and (f) a suitable buffer, under conditions that are effective for joining the two or more DNA molecules to form a first assembled dsDNA molecule in a one-step thermocycled reaction.

In one embodiment of this aspect, the exonuclease of (a) is Exonuclease III, and/or the polymerase of (c) is heat-activated by the removal of an inactivating moiety combined with the polymerase in a heat-sensitive manner; and/or the crowding agent of (b) is PEG, and/or the ligase of (d) is Taq ligase. The DNA polymerase of (c) may be AMPLITAQ GOLD®.

This method may also be employed to obtain a second assembled set of DNA molecules that can be combined with a first assembled set. Any combination of the thermocycled one-step method and the foregoing isothermal method may be used for assembly of various sets of DNA molecules and any of the two may be used for subsequent assembly of larger DNA molecules from the assembled sets.

The components for the above method may be provided as a kit that comprises, in a single vessel: (a) an isolated non-thermostable 3' to 5' exonuclease active in the presence of dNTPs, (b) a crowding agent, (c) an isolated heat-activated DNA polymerase, (d) an isolated thermostable ligase, (e) a mixture of dNTPs, and (f) a suitable buffer, in amounts such that when said two or more DNA molecules are added to the kit, in the presence of a suitable buffer solution and dNTPs, and incubated under thermocycled conditions, the two or more DNA molecules are assembled in a concerted reaction. In one embodiment of this aspect, the kit comprises: (a) Exonuclease III, (b) PEG, (c) AMPLITAQ GOLD® DNA polymerase, and (d) Taq ligase.

Any combination of materials useful in the disclosed methods of the first and second aspects can be packaged together as a kit for performing any of the disclosed methods. For example, a kit can comprise a mixture containing all of the reagents necessary for assembling ssDNA molecules (e.g., oligonucleotides) or dsDNA molecules.

In a third aspect, the invention provides a method of modifying the properties of a whole nucleic acid molecule. The method comprises: (a) representationally dividing the nucleic acid sequence of said whole nucleic acid molecule into a multiplicity of portions along its length thereby identifying the sequences of partial nucleic molecules; (b) providing, for at least 3 of said partial nucleic molecules, a multiplicity of variants of each partial nucleic acid molecule; (c) combinatorially assembling in vitro said variants along with any partial nucleic acid molecules which are not varied, wherein the partial nucleic acid molecules or variants thereof contain overlapping sequences at their termini whereby assembly of the partial nucleic acid molecules and variants thereof in the mixture would result in assembly of a multiplicity of variants of the whole nucleic acid molecule; and (d) expressing the variants of the whole nucleic acid molecule to determine any modified properties of said variants of said whole nucleic acid molecule.

The assembling of step (c) may be performed by either of the foregoing methods, although alternative joining methods may also be used. Multistep in vitro methods may be used, for example, or in vivo methods, such as those described in PCT application PCT/US2008/079109 (WO 2009/048885) may be used. While in vitro assembly methods are generally more convenient for oligonucleotides, in vivo assembly methods are also workable alternatives.

One assembly method that may be employed comprises the steps of: (a) contacting said variants along with any partial nucleic acid molecules which are not varied with a non-processive 5' exonuclease; and with (b) a single stranded DNA binding protein (SSB) which accelerates nucleic acid annealing; and with (c) a non-strand-displacing DNA polymerase; and with (d) a ligase, under conditions effective to join the variants and partial nucleic acid molecules that are not varied so as to result in assembly of a multiplicity of variants of the whole nucleic acid molecule.

This aspect, in one embodiment, comprises dividing the nucleic acid sequence of the whole nucleic acid molecule into at least 5 portions which can advantageously be assembled using the in vitro methods of the invention. In other embodiments, the partial nucleic acid molecular variants provide degenerate forms of the codon for one or more amino acids encoded by the partial nucleic acid molecules. Alternatively, the variants of the partial nucleic acid molecule provide a multiplicity of nucleic acid control sequences affecting transcription or translation of the whole nucleic acid molecule. As another alternative, the variants of the partial nucleic acid molecule provide a multiplicity of regions encoding domains or motifs of peptides or proteins encoded by the whole nucleic acid molecule. As yet another alternative, the peptides or proteins encoded by said partial nucleic acid molecules function together in a metabolic pathway.

The various recombination approaches set forth above can be used to construct any desired assembly, such as plasmids, vectors, genes, metabolic pathways, minimal genomes, partial genomes, genomes, chromosomes, extrachromosomal nucleic acids, for example, cytoplasmic organelles, such as mitochondria (animals), and in chloroplasts and plastids (plants), and the like. For the assembly of large DNA molecules, the final steps may be conducted in vivo, where yeast is a preferred host. The balance between in vitro and in vivo conduct of assembly steps is determined by the practicality of the method with regard to the nature of the DNA molecules to be assembled.

The invention further includes libraries of DNA molecules obtained by the foregoing methods, and methods to use the modified whole DNA molecules. The libraries, which contain 2 or more variants, but typically multiple variants, such as 20, 100, 1000 or more can be screened for members having desired characteristics, such as high production levels of desired products, enhanced functionality of the products, or decreased functionality (if that is advantageous). Such screening may be done by high throughput methods, which may be robotic/automated.

The invention also further includes products made by the methods of the present invention, for example, the resulting assembled synthetic genes or genomes and modified optimized genes and genomes, and the use and products thereof.

The recombinant methods of the invention have a wide variety of applications, permitting, for example, the design of pathways for the synthesis of useful products, including pharmaceuticals, biofuels, diagnostics, veterinary products, agricultural chemicals, growth factors, and the like—i.e., any molecule that can be assembled in a cell culture or in a transgenic animal or plant. As a simple example, the acetate pathway of *E. coli* can be adapted to produce biofuels such as ethanol, butanol and the like. Enzymes on a synthetic pathway for a secondary metabolite, such as a polyketide, can also be optimized using the methods of the invention. Thus, the DNA molecules that result from the systemic combinatorial procedures of the invention may be employed in a wide variety of contexts to produce useful products.

BRIEF DESCRIPTION OF THE DRAWINGS

FIG. 2A is a schematic of the strategy used to analyze the success of a repaired assembly reaction. dsDNA is denatured to ssDNA in the presence of formamide (+F), and ssDNA remains intact with a higher molecular weight if repair has occurred.

FIG. 2B shows the results of the method of FIG. 2A used to analyze products assembled using the method shown in FIG. 1A.

FIG. 3 shows the results of rolling circle amplification (RCA) of repaired assembly products joining 4 DNA fragments, showing that only repaired assembly products are amplified.

FIG. 5A is a schematic of a one-step isothermal in vitro assembly using T5 exonuclease.

FIG. 5B shows the results of assembly of 2 nucleic acid fragments, 4,024 bp and 2,901 bp, with ~450 bp overlapping sequences, using the method shown in FIG. 5A, and incorporating a NotI restriction enzyme sequence.

FIG. 5C shows the results of NotI digestion of the product shown in FIG. 5B.

FIG. 5D shows the results of assembly of 3 nucleic acid fragments, each ~5 kb, together with a vector sequence of ~8 kb, with 40 bp overlapping sequences, using the method shown in FIG. 5A.

FIG. 5E shows representative results of DNA purified from *E. coli* transformed with the assembly product shown in FIG. 5D, and digested with Not I to release the assembled fragments from the vector.

FIG. 6A shows the results of assembly of 4 nucleic acid fragments, 5.9 kb to 6.2 kb, with 80 bp overlapping sequences, together with a vector of ~8 kb with 80 bp overlapping sequences, using the various assembly methods described above.

FIG. 6B shows representative results of DNA purified from *E. coli* transformed with the assembly products shown in FIG. 6A, and digested with NotI to release the assembled fragments from the vector.

FIG. 6C shows the results of assembly of 2 one-quarter genomes of *Mycoplasma genitalium*, together with a vector of ~8 kb with 80 bp overlapping sequences, using the various assembly methods described above.

FIG. 6D shows representative results of DNA purified from *E. coli* transformed with the assembly products shown in FIG. 6C, and digested with NotI to release the assembled fragments from the vector.

FIG. 9A shows the results of assembly of five 300 bp fragments, in 15 reactions covering the entire mouse mitochondrial genome.

FIG. 9B shows the results of amplification of the reaction products shown in FIG. 9A.

FIG. 9C shows the results of assembly of five 1,180 bp products of the reaction shown in FIG. 9A, in 3 reactions covering the entire mouse mitochondrial genome.

FIG. 9D shows the results of amplification of the reaction products shown in FIG. 9C.

FIG. 9E shows the results of the final assembly of the whole mouse mitochondrial genome from three 5,560 bp products of the reaction shown in FIG. 9C, in a vector construct.

FIG. 9F shows the results of the final assembly of the whole mouse mitochondrial genome product shown in FIG. 9F after removal of the vector sequence and recircularization.

DETAILED DESCRIPTION OF THE INVENTION

Figure 1A:
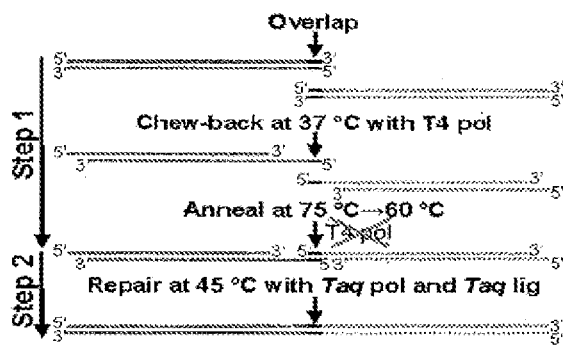
FIG. 1A is a schematic of a two-step thermocycled in vitro assembly using T4 polymerase.
Figure 1C:
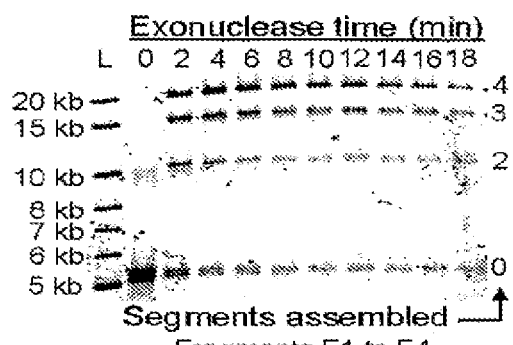
FIG. 1C shows the results of assembly of 4 nucleic acid fragments, each 5 kb, with 40 bp overlapping sequences, in the presence of PEG-8000, using the method shown in FIG. 1A.
Figure 1B:
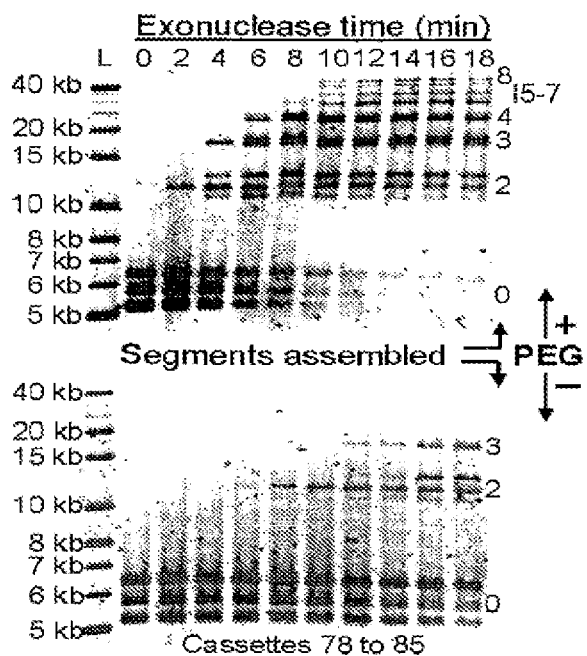
FIG. 1B shows the results of assembly of 8 nucleic acid fragments, each between 5.3 kb and 6.5 kb, with 240 to 360 bp overlapping sequences, carried out in the presence (+) or absence (−) of 5% PEG-8000, using the method shown in FIG. 1A.
Figure 1D:
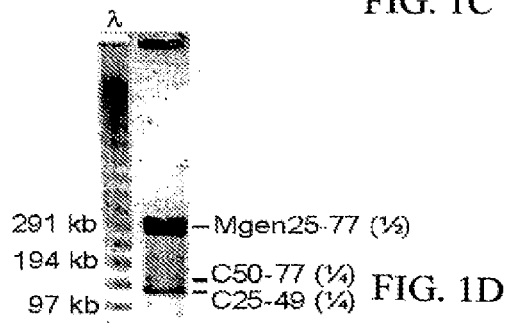
FIG. 1D shows the results of assembly of a *Mycoplasma genitalium* one-half genome (310 kb), from two one-quarter genome fragments, 144 kb and 166 kb, with 257 bp overlapping sequences.
Figure 1E:
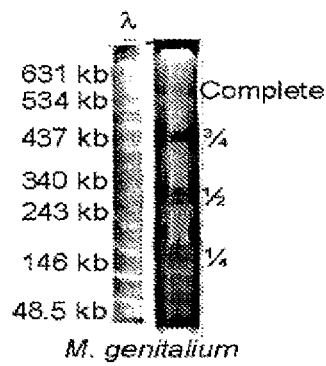
FIG. 1E shows the results of assembly of the complete synthetic *Mycoplasma genitalium* genome from four one-quarter genome fragments, ~150 kb each with 80 to 257 bp overlapping sequences.
Figure 4A:
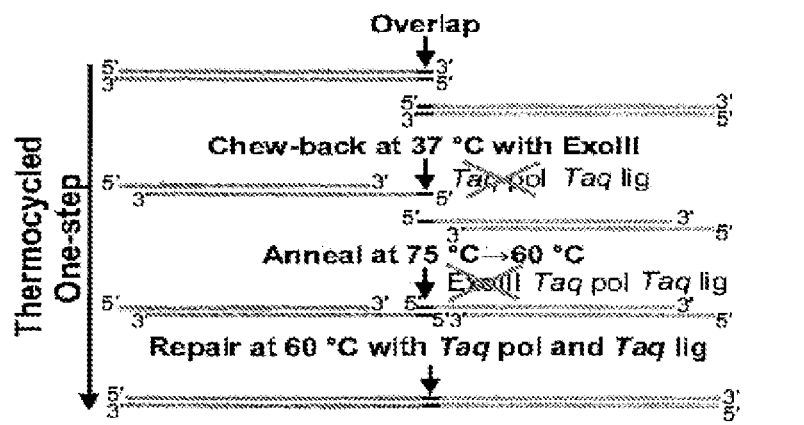
FIG. 4A is a schematic of a one-step thermocycled in vitro assembly using exonuclease III.
Figure 4B:
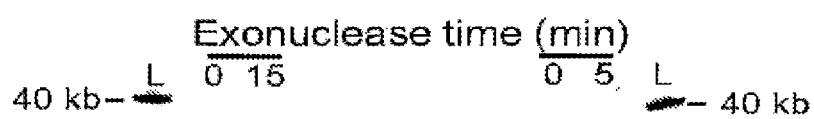
FIG. 4B shows the results of 2 assemblies of 4 different nucleic acid fragments, each ~5 kb with either 300 bp or 40 bp overlapping sequences, using the method shown in FIG. 4A.
Figure 4C:
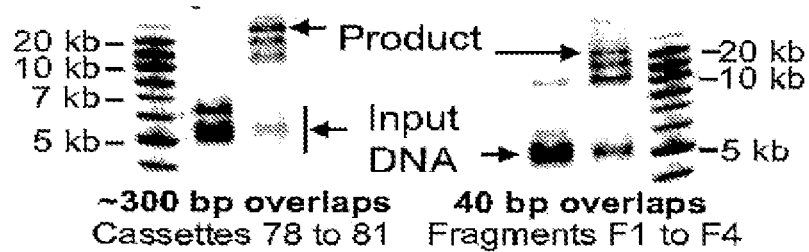
FIG. 4C shows the results of analyzing the repair of the assembly products, as shown in FIG. 2A.
Figure 6A:
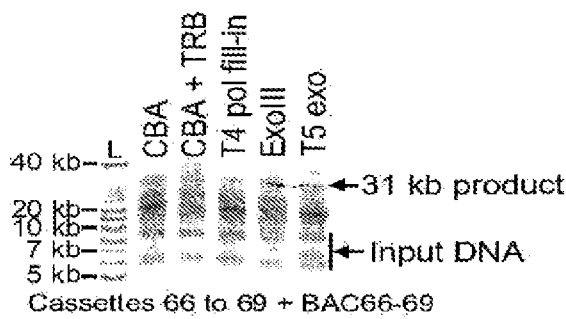
FIGS. 6A-6D show the results of direct comparisons of the methods shown in FIG. 1A (T4 polymerase), FIG. 4A (exonuclease III) and FIG. 5A (T5 exonuclease).
Figure 6C:
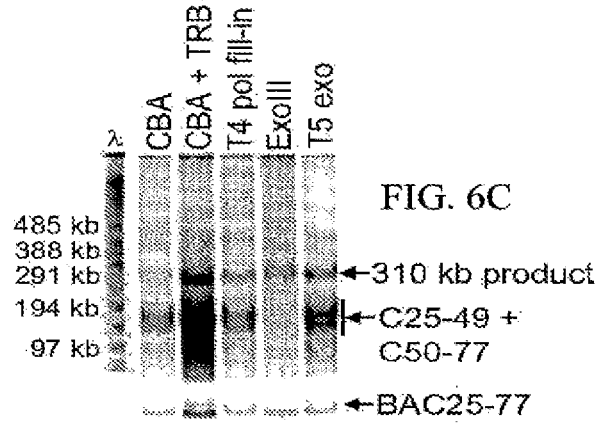
Figure 6B:
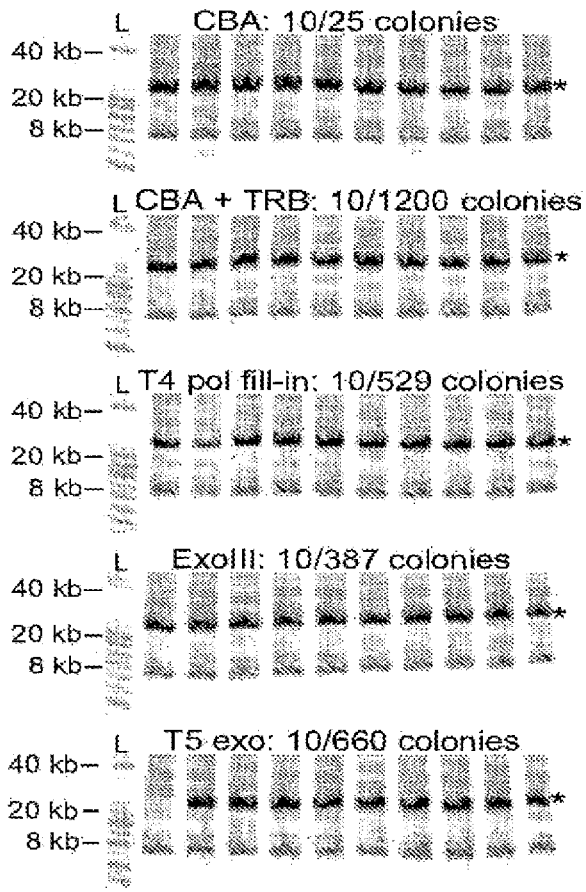
Figure 6D:
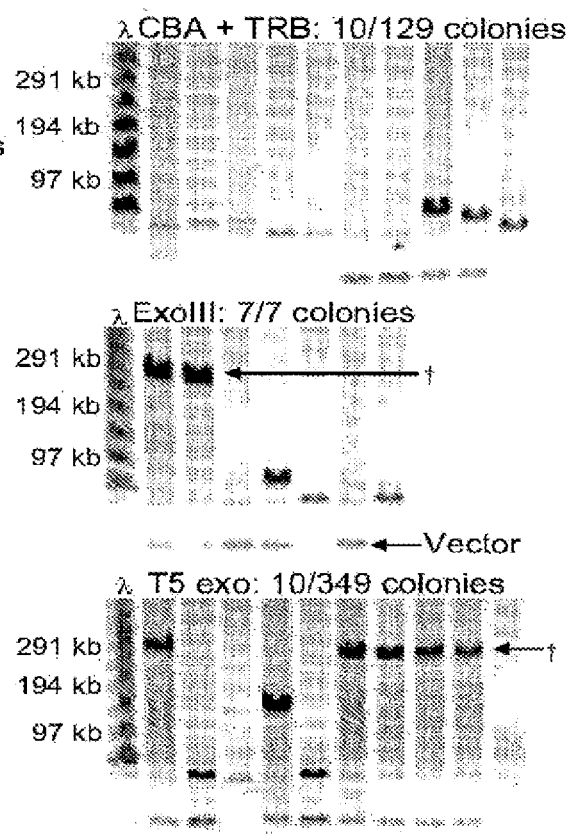

Modes of Carrying Out the Invention
Definitions

As used herein, the singular forms "a," "an," and "the" include plural referents unless the context clearly dictates otherwise.

The term "about," as used herein, refers to plus or minus 20%. Thus, "about" 30 minutes includes 24-30 minutes. "About" also refers to plus or minus 20% when referring to lengths of nucleic acids, temperatures, etc. The end points of ranges, as used herein, are included in the range. When plus or minus 20% results in a non-integral value of indivisible units, such as nucleotides, a skilled worker will recognize that one should round the value to the nearest integer. For example, about 8 nucleotides is not 6.4 to 9.6 nucleotides, but should be interpreted as 6 to 10 nucleotides.

The term "activity temperature" refers to the temperature above which the DNA polymerase is sufficiently more active than the exonuclease (i.e., exonuclease III) such that there is a net reduction in the length of the single-strand overhangs created initially by the exonuclease (i.e., exonuclease III).

In those methods of the invention that are carried out "in vitro", all of the protein components are isolated and/or substantially purified. The in vitro assembly reactions are not carried out in a living cell or with a crude cell extract; the reactions are carried out in a cell-free environment.

The "joining" of DNA molecules by a method of the invention is sometimes referred to herein as "recombination" or "assembly" of the DNA molecules.

According to the present invention, optimization at the genetic level is achieved in a systematic manner by design of discrete components. This is true at all levels of combination as described above. The invention methods thereby avoid the random nature of prior art approaches.

Methods of Nucleotide Assembly

In brief, when the DNA molecules to be joined are double-stranded, the preferred method comprises incubating the DNA molecules with (a) an exonuclease (e.g., a non-processive exonuclease), which "chews-back" the ends of the double-stranded DNA molecules, to expose single-stranded overhangs comprising the regions of overlap; (b) a crowding agent, such as PEG, which, among other functions, accelerates nucleic acid annealing, so that the single-stranded overhangs are annealed (hybridized) specifically; (c) a non-strand-displacing DNA polymerase, which fills in remaining single-stranded gaps in the annealed molecules, by extending the 3' ends of the annealed regions; and (d) a thermostable ligase, which seals (ligates) the nicks thus formed. For single-stranded molecules, the exonuclease of (a) may be, but need not be, omitted.

When the DNA molecules to be joined are single-stranded, the single-stranded DNA molecules (e.g., oligonucleotides of about 40-60 bases, also referred to herein as nucleotides or nt) anneal via the sequences of identity at their ends (e.g., about 20 bases), to form gapped molecules. The exonuclease activity may act on these gapped molecules to increase the size of the gap. The gapped molecules are then repaired with the polymerase and the ligase, as above, to form double stranded molecules.

The novel one-step methods of the invention can be used to simultaneously join a large number of DNA molecules. To accomplish this, the DNA molecules to be joined are designed so that, for each pair of DNA molecules to be joined contain overlapping sequences at their termini—i.e., the distal region of one DNA molecule comprises a region of unique sequence homology (e.g., identity) with the proximal region of the other DNA molecule. Distal and proximal refer to an arbitrary reference point at one end of a chain of molecules, e.g., with respect to the referent X,

A represents a proximal and B represents a distal region. To facilitate the joining of the DNA molecules in a predetermined orientation and order, each set of distal and proximal regions of sequence identity is selected (designed) to be unique (to be different from the regions of sequence identity of the other pairs of DNA molecules). The method allows a number of DNA molecules to be joined in a single reaction mixture, and in a single vessel. It will be evident that the regions of homology are, in some circumstances, complementary. The term a "region of sequence identity" encompasses both identical and complementary sequences.

In methods of the invention, the distal region of one of a pair of dsDNA molecules to be joined shares a region of sequence homology (e.g., sequence identity) with the proximal region of the other dsDNA molecule. The term "distal" as used herein refers to the 3' end of a first DNA molecule of a pair to be joined (the 5'-most DNA molecule), and the term "proximal" refers to the 5' end of the second DNA molecule of the pair. The regions of homology are sometimes referred to herein as "overlaps", "overlapping sequences", or "regions of overlap." A "region of sequence homology (identity)", as used herein, refers to both strands of the double-stranded DNA molecule. Thus, one strand from this region can hybridize specifically to its complementary strand, e.g., when the complementary regions are present in single-stranded overhangs from the distal and proximal regions of the two molecules to be joined.

In one embodiment, the DNA molecules which are joined are synthetically generated DNA molecules that may lie adjacent to one another in a gene or genome of interest. For example, a first set of about eight 60-mer single-stranded oligonucleotides (oligos) having 20 base regions of sequence identity at either end may be joined in the proper order and orientation to form a dsDNA of 300 bp. A second set of a similar number of adjoining DNA molecules of about the same size may also be joined; and then, in a second stage assembly, the two sets of joined molecules are joined to one another. The process is repeated with further sets of DNA molecules, in as many cycles as desired. In such a manner, the component elements of a gene or genome, all or nearly all of which have been generated synthetically, can be joined in sequential steps to form a complete gene or genome.

Advantages of the method of the invention include the ability to perform the joining reactions under well-defined conditions, using well-characterized, isolated (e.g., substantially purified) enzymes. This allows the joining reactions to be controlled and reproducible. In a method of the invention, the joining process is not subject to competing reactions brought about by other enzymes in the reaction mixture, such as exonucleases and endonucleases which can be present in cells or cell extracts. The joining methods of the invention are accurate, inexpensive, require very little sample handling, and can be completed rapidly (e.g., between about 15 minutes and an hour, such as between about 15 and about 30 minutes) in single vessel. If desired, the steps of the method can be carried out robotically, without the intervention of an investigator.

Other advantages of a method of the invention include the following: the ability to join DNA molecules in a defined order and orientation allows, for example, for the cloning of one or more fragments of interest into a linearized vector in a defined orientation; or for the assembly of component DNA portions of a longer sequence of interest (such as the assembly of component parts of a synthetic gene or genome); or for the assembly and cloning of sub-fragments of a DNA which are too large to clone using a PCR amplification step. The method allows one to join and/or clone DNA molecules of interest without having to rely on the presence of restriction enzyme recognition sites at the ends of the fragments to be joined. The in vitro procedure also allows one to assemble DNAs that are unstable or otherwise recalcitrant to in vivo cloning, and thus would be difficult to clone by a method requiring transformation into and replication in a bacterium. If desired, DNAs assembled by a method of the invention can then be amplified in vitro (e.g., by multiple displacement amplification (MDA), such as rolling circle amplification (RCA); or by PCR), again without having to passage the DNA through a bacterium. If desired, DNA molecules can be assembled in the presence of vector, so that the cloned sequence can be transformed into a suitable host cell directly after the assembly is complete.

These methods can be repeated sequentially, to assemble larger and larger molecules. For example, a method of the invention can comprise repeating a method as above to join a second set of two or more DNA molecules of interest to one another, and then repeating the method again to join the first and second set DNA molecules of interest, and so on. At any stage during these multiple rounds of assembly, the assembled DNA can be amplified by transforming it into a suitable microorganism, or it can be amplified in vitro (e.g., with PCR or rolling circle amplification (RCA)).

In one aspect of the invention, the DNA molecules of interest are single-stranded oligonucleotides that are about 40-60 bases in length, and the region of sequence identity consists of no more than 20 bases. In other aspects of the invention, the DNA molecules of interest are double-stranded DNA molecules of at least about 100, 200, 500, 1,000, 5,000, 50,000, 100,000, 200,000, 500,000, or $1 \times 10^6$ bp in length. The regions of sequence identity in these dsDNA molecules may comprise at least about 20, 30 or 40 nucleotides (nt), e.g., at least about 80, 300, 500 or more nt.

The methods of the invention may be used to join at least about 8 DNA oligonucleotides (oligos), e.g., as many as about 100 oligonucleotides in a single concerted reaction, to generate one contiguous DNA. In a single vessel, many such concerted reactions can take place simultaneously. For example, in a single vessel, hundreds of reactions can be performed simultaneously, in each of which 8 oligonucleotides are assembled to form a contiguous DNA, resulting in hundreds of contiguous DNAs. For the joining of dsDNA molecules in a single concerted reaction, there may at least about 4 (e.g., at least about 5, 10, 25, 50, 75 or 100 molecules), wherein for each pair of molecules to be joined, the distal region of one DNA molecule comprises a region of sequence homology to the proximal region of the other DNA molecule, and each set of distal and proximal regions of homology is unique for each pair of DNA molecules to be joined.

In a joining reaction of the invention, the collection of DNA molecules of interest to be joined can further comprise a linearized vector DNA molecule, and the joined DNAs of interest can thus be cloned into the vector. Such molecules can, if desired, be transformed into a host cell (e.g., a microorganism, such as a bacterium (e.g., E. coli), yeast or a eukaryotic cell, such as a mammalian cell).

In methods of the invention, one or more (e.g., all) of the DNA molecules can be generated synthetically. The DNA molecules may be adjacent sequences of a gene or genome of interest. In one embodiment, the DNA molecules are synthesized so as to comprise overlapping regions of sequence identity at their ends, and the DNA molecules are joined to form part or all of a synthetic gene or genome.

In one aspect of the invention, each of the DNA molecules of interest to be joined comprises, at the free end of each of the two regions of identity, a sequence that is non-homologous to any of the DNA molecules of interest; and during the joining reaction, the non-homologous sequences are removed by the 3' exonuclease activity of the polymerase (for the isothermal method) or the 5' exonuclease activity of the polymerase for the thermocycled method. The non-homologous sequences may comprise one or more binding domains for PCR primers (e.g., four different binding domains), and/or recognition sites for one or more restriction enzymes.

Thus, methods of the invention can be readily adapted to be automated and high throughput (e.g., carried out by robotic methods).

Chew-Back

In methods of the invention, the exonuclease digestion is carried out under conditions that are effective to chew-back a sufficient number of nucleotides to allow for specific annealing of the exposed single-stranded regions of homology. In general, at least the entire region of overlap is chewed back, leaving overhangs which comprise the region of overlap. In some methods, the exonuclease digestion may be carried out by a polymerase in the absence of dNTPs (e.g., T5 DNA polymerase) while in other methods, the exonuclease digestion may be carried out by an exonuclease in the presence of dNTPs that lacks polymerase activity (e.g., exonuclease III).

In other embodiments, e.g., when the region of overlap is very long, it may only be necessary to chew-back a portion of the region (e.g., more than half of the region), provided that the single-stranded overhangs thus generated are of sufficient length and base content to anneal specifically under the conditions of the reaction. By "annealing specifically" is meant herein that a particular pair of single-stranded overhangs will anneal preferentially (or only) to one another, rather than to other single-stranded overhangs which are present in the reaction mixture. By "preferentially" is meant that at least about 95% of the overhangs will anneal to the paired overhang. A skilled worker can readily determine the optimal length for achieving specific annealing of a sequence of interest under a given set of reaction conditions. Generally, the homologous regions of overlap (the single-stranded overhangs or their complements) contain identical sequences. However, partially identical sequences may be used, provided that the single-stranded overhangs can anneal specifically under the conditions of the reactions.

Crowding Agent

A suitable amount of a crowding agent, such as PEG, in the reaction mixture allows for, enhances, or facilitates molecular crowding. Without wishing to be bound by any particular mechanism, it is suggested that a crowding agent, which allows for molecular crowding, binds to and ties up water in a solution, allowing components of the solution to come into closer contact with one another. For example, DNA molecules to be recombined can come into closer proximity; this thus facilitates the annealing of the single-stranded overhangs. Also, it is suggested that enzymes can come into closer contact with their DNA substrates and can be stabilized by the removal of water molecules. A variety of suitable crowding agents will be evident to the skilled worker. These include a variety of well-known macromolecules, such as polymers, e.g., polyethylene glycol (PEG); FICOLL®, such as FICOLL® 70; dextran, such as dextran 70; or the like. Much of the discussion in this application is directed to PEG. However, the discussion is meant also to apply to other suitable crowding agents. A skilled worker will recognize how to implement routine changes in the method in order to accommodate the use of other crowding agents.

In general, when PEG is used, a concentration of about 5% (weight/volume) is optimal. However, the amount of PEG can range, e.g., from about 3 to about 7%. Any suitable size of PEG can be used, e.g., ranging from about PEG-200 (e.g., PEG-4000, PEG-6000, or PEG-8000) to about PEG-20,000, or even higher. In the Examples herein, PEG-8000 was used. The crowding agent can, in addition to enhancing the annealing reaction, enhance ligation.

Gap Repair

Following the annealing of single stranded DNA (either overhangs produced by the action of exonuclease when the DNA molecules to be joined are dsDNA, or the regions of sequence identity of single stranded DNA molecules when the DNAs to be joined are single-stranded DNA), the single-stranded gaps left by the exonuclease are filled in with a suitable thermostable, non-strand-displacing, DNA polymerase (sometimes referred to herein as a "polymerase") and the nicks thus formed a sealed with a thermostable ligase. A "non-strand-displacing DNA polymerase," as used herein, is a DNA polymerase that terminates synthesis of DNA when it encounters DNA strands which lie in its path as it proceeds to copy a dsDNA molecule, or that degrades the encountered DNA strands as it proceeds while concurrently filling in the gap thus created, thereby generating a "moving nick" (nick translation).

The nicks generated by the gap-filling reaction can be sealed with any of a variety of suitable thermostable DNA ligases (sometimes referred to herein as "ligases"). Among the suitable ligases are, for example, Taq ligase, Ampligase Thermostable DNA ligase (Epicentre Biotechnologies), the Thermostable ligases disclosed in U.S. Pat. No. 6,576,453, Thermostable Tfi DNA ligase from Bioneer, Inc., etc.

Generally, substantially all of the nicks (or all of the nicks) are sealed during the reaction procedure. However, in one embodiment, joined DNA which still comprises some nicks can be transformed into a bacterium, such as E. coli, where the nicks are sealed by the bacterial machinery.

The amount of the enzymes used in a method of the invention can be determined empirically. Generally, the amount of 5' exonuclease activity is substantially lower than the amount of the polymerase activity, and ligase activity is in large excess over the polymerase. Suitable amounts of enzymes to be used in a method of the invention are illustrated in the Examples herein.

Reaction components (such as salts, buffers, a suitable energy source (such as ATP or NAD), pH of the reaction mixture, etc.) that are present in a reaction mixture of the invention may not be optimal for the individual enzymes (exonuclease, polymerase and ligase); rather, they serve as a compromise that is effective for the entire set of reactions. Some exemplary reaction conditions are presented in the Examples. For example, one suitable buffer system identified by the inventors, sometimes referred to herein as ISO (ISOthermal) Buffer typically comprises 0.1 M Tris-Cl pH 7.5; 10 mM $MgCl_2$, 0.2 mM each of dGTP, dATP, dTTP and dCTP, 10 mM DTT, 5% PEG-8000, and 1 mM NAD.

In a method of the invention, the proteins having exonuclease, polymerase and ligase activities are isolated (e.g., substantially purified); cell extracts or intact cells are not employed. The term, an "isolated" protein, as used herein, means that the protein is removed from its original environment (e.g., the natural environment if it is naturally occurring), and isolated or separated from most other component with which it is naturally associated. For example, a naturally-occurring protein present in its natural living host (e.g., a bacteriophage protein present in a bacterium that has been infected with the phage) is not isolated, but the same protein, separated from some or all of the coexisting materials in the natural system, is isolated. Such proteins can be part of a composition or reaction mixture, and still be isolated in that such composition or reaction mixture is not part of its natural environment. The term "an isolated protein," as used herein, can include 1, 2, 3, 4 or more copies of the protein, i.e., the protein can be in the form of a monomer, or it can be in the form of a multimer, such as dimer, trimer, tetramer or the like, depending on the particular protein under consideration. In some embodiments, the protein is purified. Methods for purifying the proteins used in methods of the invention are conventional. In some embodiments, the protein is substantially purified or is purified to homogeneity. By "substantially purified" is meant that the protein is separated and is essentially free from other proteins, i.e., the protein is the primary and active constituent. The purified protein can then be contacted with the DNAs to be joined. Proteins used in the methods of the invention can be in the form of "active fragments," rather than the full-length proteins, provided that the fragments retain the activities (enzymatic activities or binding activities) required to achieve the joining. One of skill in the art will recognize how to make and use such active fragments.

Joining DNA Molecules

In methods of the invention, at least two DNA molecules are contacted with the enzymes under conditions effective to join the DNA molecules to form a substantially intact (preferably having no nicks) double-stranded DNA molecule (e.g., in which a single copy of the region of sequence identity is retained).

A method of the invention can be used to join any DNA molecules of interest, including DNAs which are naturally occurring, cloned DNA molecules, synthetically generated DNAs, etc. The joined DNA molecules may, if desired, be cloned into a vector (e.g., using a method of the invention).

DNA molecules of any length can be joined by methods of the invention. Single-stranded oligonucleotides of about 40-60 bases can be joined, e.g., via overlaps of about 20 bases. The minimum size for joining molecules with a 40 bp overlap is about 80 bp. For molecules with a 200 bp overlap, the minimum size is about 400 bp. Theoretically, there should be no maximum size of DNA molecules that can be joined (although very large molecules would be more fragile than smaller ones, and thus subject to possible breakage). For example, cassettes having about 100 bp to about 750 or 1,000, or more, can be joined.

From two to an essentially unlimited upper level of DNA molecules can be joined. In general, at least about 5-10 fragments can be joined. The number of fragments which can be joined depends, in part, on the length of the overlaps and the lengths of the fragments. For example, with fragments having overhangs of about 150 to about 200 bp (e.g., fragments of about 3 kb, or larger or smaller), the number of fragments that can be joined is substantially unlimited. The number of fragments that can be joined in one reaction also depends, in part, on the efficiency of the joining process. If the efficiency of joining is 100%, then an infinite number of DNA molecules could theoretically be joined (provided that an approximately equal number of molecules of each substrate is present in the reaction). With lower efficiencies (e.g., about 75-90% joining of each pair of two molecules), two to about 250 DNA molecules can be joined. Methods of the invention work well with a wide range of substrate DNA (e.g., about 10 to about 1,000 ng of each substrate in a reaction mixture.)

In some embodiments of the invention, the joined DNA molecules form a circle and/or become ligated into a vector to form a circle. The lower size limit for a dsDNA to circularize is about 200 base pairs. Therefore, the total length of the joined fragments (including, in some cases, the length of the vector) is preferably at least about 200 bp in length. There is no practical upper size limit, and joined DNAs of a few hundred kilobase pairs, or larger, can be generated by a method of the invention. The joined DNAs can take the form of either a circle or a linear molecule.

More particularly, the number of DNA molecules or cassettes that may be joined in vitro to produce an end product, in one or several assembly stages according to the invention, may be at least or no greater than about 2, 3, 4, 6, 8, 10, 15, 20, 25, 50, 100, 200, 500, 1,000, or 10,000 DNA molecules, for example in the range of about 4 to about 100 molecules. The number of assembly stages may be about 2, 4, 6, 8, 10, or more. The number of molecules assembled in a single stage may be in the range of about 2 to about 10 molecules. The methods of the invention may be used to join together DNA molecules or cassettes each of which has a starting size of at least or no greater than about 40 bs, 60 bs, 80 bs, 100 bs, 500 bs, 1 kb, 3 kb, 5 kb, 6 kb, 10 kb, 18 kb, 20 kb, 25 kb, 32 kb, 50 kb, 65 kb, 75 kb, 150 kb, 300 kb, 500 kb, 600 kb, 1 Mb, or larger, for example in the range of about 3 kb to about 500 kb. The DNA end products of the inventive methods may be at least about 500 bs, 1 kb, 3 kb, 5 kb, 6 kb, 10 kb, 18 kb, 20 kb, 25 kb, 32 kb, 50 kb, 65 kb, 75 kb, 150 kb, 300 kb, 500 kb, 600 kb, 1 Mb, or larger, for example in the range of 30 kb to 1 Mb. In one embodiment, the inventive methods are used for the in vitro assembly of short single-stranded oligonucleotides, through several rounds of assembly, into cassettes of about 6 kb, and then the assembly of 100 such cassettes into a DNA molecule of about 600 kb.

When joining a mixture of DNA molecules, it is preferable that the DNAs be present in approximately equimolar amounts. If the number of DNA molecules is not balanced, the result would be a termination of assembled species. For example, consider an example in which 8 DNA molecules are to be assembled (numbered 1-8). If, for example, there was an excess of molecule number 4, the majority of assembled molecules would be 1-4 and 4-8. Assuming only a few hundred bases is being chewed back in the reaction, there would be no sequence homology between the distal region of 1-4 and the proximal region of 4-8, thereby decreasing the amount of 1-8.

Region of Sequence Homology

The region of sequence identity should be sufficiently long to allow specific recombination to occur. That is, it should be long enough so that the region of overlap at the ends of two DNA molecules to be joined is unique to those DNA molecules, and no other DNA molecules will anneal to those two DNA molecules during the recombination reaction. The length can vary from a minimum of about 10 base pairs (bp) to about 300 bp or more. In general, it is preferable that the length of the overlap is less than or equal to about the size of the fragment to be combined, but not less than about 10 bp and not more that about 1000 bp. For the joining of 2 or 3 fragments, about 20-30 bp overlap may be sufficient. For more than 10 fragments, a preferred overlap is about 80 bp to about 300 bp. In one embodiment, the region of sequence identity is of a length that allows it to be generated readily by synthetic methods, e.g., about 40 bp (e.g., about 32 to about 48 bp). The overlaps may be, e.g., about 10, 20, 30, 40, 50, 60, 70, 80, 90, 100, 150, 200, 250, 300, 350, 400, 450, 500, 550, 600, 650, 700, 750, 800, 850, 900, 950 or 1,000 bp in length.

In a preferred embodiment, when a plurality of DNA molecules are to be joined, for each pair of DNA molecules to be joined, the distal region of one of the DNA molecules of the pair is designed to share a region of sequence identity with the proximal region of the other DNA molecule of the pair, and the distal and proximal regions of sequence identity for each pair of DNA molecules are designed to be unique (to be different from the regions of sequence identity of the other pairs of DNA molecules). When the overlapping regions of identity are designed in this manner, the orientation and order of the DNA molecules in the joined molecule can be predetermined. A number of DNA molecules (for example, 4 or 6 molecules) can thus be incubated together in a single reaction mixture (in a single vessel or container) in a method of the invention, and be joined into a longer DNA molecule in which the individual DNAs are arranged in any desired order and orientation.

The regions of sequence identity present in the proximal and distal regions of the DNAs to be joined can be generated by any of a variety of methods.

For example, in one embodiment of the invention, synthetically prepared, overlapping fragments of a gene or genome of interest (e.g., about 5-6 kb in length, or longer or shorter) are optionally amplified (e.g., by PCR, or by MDA such as a rolling circle mechanism) and are joined by a method of the invention in the order and orientation in which they are located in the gene or genome. In this method, the first DNA fragment (e.g., in the 5' most portion of the gene or genome) is synthesized so that the region at its 3' end (the distal end) contains a sequence (e.g., about 40 bp) that is identical to the sequence at the 5' end (the proximal end) of the DNA fragment to which it is to be joined. The second DNA fragment, in turn, is synthesized so that it has, at its distal end, a sequence which is identical to the sequence at the proximal end of the third DNA fragment, and so on. In another embodiment, synthetically prepared fragments of a gene or genome of interest are inserted into a vector, propagated in *E. coli* to make more of the synthetically prepared fragment, then released from the vector, optionally amplified further by PCR, MDA or RCA, and joined by a method of the invention in the order and orientation in which they are located in the gene or genome. These procedures allow the preparation of a synthetic gene or genome.

In another embodiment of the invention, two fragments to be joined are generated by restriction enzyme digestion, such that the fragments overlap one another, e.g., by about 20 to about 1,000 bp. The overlapping regions can then be joined by a method of the invention. Greater numbers of fragments can also be generated by these methods and joined. Combinations of the preceding method and methods using synthetically prepared DNA molecules and/or molecules generated by PCR can be used.

In one embodiment of the invention, chemically synthesized oligonucleotides, from about 20 bp to any size that can be synthesized chemically, can be used. For example, 10 ssDNA oligonucleotides of about 60 bp, having about 10-20 bp homology overlap at each end, can be assembled simultaneously into a vector. The assembly of 10 such oligonucleotides results in a dsDNA molecule of about 500 bp. DNA molecules assembled by this method can, in turn, be joined to one or more other DNA molecules assembled by this (or another) method (for example, assemblies of about 500 bp). Repetitions of the method can generate very large molecules of DNA; there is no theoretical limit to the size of a DNA molecule thus generated.

In embodiments of the invention, the regions of identity are introduced by PCR amplification.

In one such method, a fragment of interest is inserted into a vector. For example, a plasmid vector can be linearized with a restriction enzyme, generating a sequence A (e.g., having 40 bp) to the left of the restriction enzyme cut and a sequence B (e.g., having 40 bp) to the right of the restriction enzyme cut. The fragment to be cloned into the vector is PCR amplified, using PCR primers which will introduce sequence A at the left end of the fragment, and sequence B at the right end of the fragment. The regions of sequence identity (in this example, each having 40 bp) allow the fragment to be joined to the vector in a desired orientation, to form a circular molecule. Alternatively, particularly when it is desirable to avoid errors which might be introduced into an insert during PCR amplification, the vector can be PCR amplified in order to introduce at the ends of a cloning site sequences which overlap sequences at the ends of the insert. The methods described above allow for the directional cloning of any insert of interest, without having to rely on the presence of, or introduction of, restriction enzyme sites on the insert.

In a variation of the preceding method, two or more DNA fragments are joined to one another to form a linear molecule. In this variation of the preceding method, regions of sequence identity that are unique to each pair of fragments to be joined are introduced into the fragments by PCR amplification, using suitable primers. For each DNA fragment to be joined to another fragment, a sequence is introduced to the 3' (distal) end of the first fragment which overlaps with the sequence at the 5' (proximal) end of the fragment to which it is to be joined. As in the preceding method, PCR primers are used in which the regions of sequence identity (e.g., 40 nt) lie 5' to a PCR primer (e.g., having 20 nt). After a suitable number of rounds of PCR amplification, DNA fragments are produced in which defined regions of sequence identity are present at the ends of the fragments. The resulting fragments can then be joined in a predetermined order and orientation by a method of the invention.

If desired, the joined, linear DNA fragments may be circularized, or they may be inserted into a vector to form a circle (simultaneously with the joining of the fragments, or subsequent to that joining). For example, a vector can be present in the joining reaction, so that the joined fragments are introduced into the vector. The efficiency of joining a large number of fragments (e.g., 6 or 8 fragments) into a vector by a method of the invention is greater than when using a method which employs compatible restriction enzyme sites. In a typical cloning experiment with restriction enzymes and T4 DNA ligase, probability is not in favor of the researcher getting multiple inserts to ligate into a vector. However, in the assembly methods of the invention, a researcher can join about 6 inserts into a vector with approximately 20-50% efficiency, or greater. Furthermore, since the efficiency is high, there is an increased ratio of recombinants to non-recombinants. The background level of non-recombinants can be reduced further by isolating a pure band by agarose gel electrophoresis (since this method produces a high enough yield to isolate a band on agarose gels) or with a sizing column. A DNA of the desired size (having the correct number of joined DNA molecules) can be isolated and introduced into a vector, e.g., using a method of the invention. If the final product is a circle, there is no need to isolate it by agarose gel electrophoresis. Rather, the sample can be treated with an enzyme such as Plasmid-Safe™ (Epicentre), an ATP-dependent DNAse that selectively hydrolyzes linear dsDNA but not circular dsDNA. If the user's application does not require a pure clone, there may be a sufficient amount of DNA without the need to transform into *E. coli* and do plasmid preparations.

In one embodiment, joined DNA molecules and/or DNA molecules inserted into vectors are introduced into a host cell, such as a bacterial or eukaryotic cell (e.g., by transformation or transfection). Alternatively, the reaction mixture comprising the joined DNA molecules can be introduced into a host cell; only those DNAs which have recombined to form circular molecules can survive in the host cell. In another embodiment, the joined fragments and/or fragments inserted into vectors are used directly, without further passage through a cell, such as a bacterial cell.

Molecular biology methods of the invention can be carried out using conventional procedures. A variety of uses for the inventive method will be evident to the skilled worker. The inventive method can be substituted for any method in which restriction enzyme digests are used to generate compatible sequences for joining DNA molecules. In one embodiment of the invention, DNA molecules that are too large to be amplified by PCR can be cloned by joining sub-fragments by a method of the invention and then inserting them into a suitable vector. Some pieces of DNA are unstable (and therefore, unclonable) in *E. coli*, especially those that are high in A+T % content. A method of the invention allows for the assembly of DNA in vitro without the need to be transformed into *E. coli*. Furthermore, phi29 DNA polymerase can be added to the reaction to amplify the circular DNA. An in vitro recombination system of the invention can be used to recombine any homologous DNAs of interest, e.g., to repair double-stranded DNA breaks or gaps, etc. Another application of the method is to introduce a mutation into a DNA. In this method, a mutation is introduced into both the upper and lower strand PCR primers, so the amplified fragments are 100% mutant; then the fragments are joined by the method of the invention.

One embodiment of the invention is to join cassettes, such as the 5-6 kb DNA molecules representing adjacent regions of a gene or genome of interest, to create combinatorial assemblies. For example, it may be of interest to modify a bacterial genome, such as a putative minimal genome or a minimal genome, so that one or more of the genes is eliminated or mutated, and/or one or more additional genes is added. Such modifications can be carried out by dividing the genome into suitable cassettes, e.g., of about 5-6 kb, and assembling a modified genome by substituting a cassette containing the desired modification for the original cassette. Furthermore, if it is desirable to introduce a variety of changes simultaneously (e.g., a variety of modifications of a gene of interest, the addition of a variety of alternative genes, the elimination of one or more genes, etc.), one can assemble a large number of genomes simultaneously, using a variety of cassettes corresponding to the various modifications, in combinatorial assemblies. After the large number of modified sequences is assembled, preferably in a high throughput manner, the properties of each of the modified genomes can be tested to determine which modifications confer desirable properties on the genome (or an organism comprising the genome). This "mix and match" procedure produces a variety of test genomes or organisms whose properties can be compared. The entire procedure can be repeated as desired in a recursive fashion.

The disclosed methods can be used to join any nucleic acid molecules of interest. The nucleic acid molecules can come from any source, including a cellular or tissue nucleic acid sample, cloned fragments or subclones thereof, chemically synthesized nucleic acids, genomic nucleic acid samples, cDNAs, nucleic acid molecules obtained from nucleic acid libraries, etc. The DNAs can be radioactively labeled or can comprise binding entities, such as biotinylated nucleotides, which can aid in the purification of the joined DNAs. If desired, the DNA molecules to be joined, or primers for adding overlapping regions of sequence identity, can be prepared synthetically. Conventional synthesis techniques include using phosphoroamidite solid-phase chemistry to join nucleotides by phosphodiester linkages. Chemistry for joining nucleotides by phosphorothioate linkages or different linkages, such as methylphosphonate linkages, can also be used. For example, the cyanoethyl phosphoramidite method can be used, employing a Milligen or Beckman System 1 Plus DNA synthesizer (for example, Model 8700 automated synthesizer of Milligen-Biosearch, Burlington, Mass. or ABI Model 380B). Synthetic methods useful for making DNA molecules are also described by Ikuta, et al., *Ann Rev. Biochem.* (1984) 53:323-356, (phosphotriester and phosphite-triester methods), and Narang, et al., *Methods Enzymol.* (1980) 65:610-620 (phosphotriester method). DNAs prepared by methods as above are available from commercial sources, such as Integrated DNA Technologies (IDT), Coralville, Iowa.

Methods of the invention are amenable to automation and to adaptation to high throughput methods, allowing for the joining of multiple DNA molecules simultaneously by computer-mediated and/or robotic methods that do not require human intervention.

DNA Modifications and Nucleotide Analogs

DNA used in a method of the invention can be modified in any of a variety of ways, provided that the modified DNA is able to function in the method. A skilled worker can readily determine if a particular modification allows the modified DNA to function (e.g., to be recognized by and acted upon by enzymes used in the method).

DNAs used in methods of the invention can have one or more modified nucleotides. For example, they may contain one or more modifications to either the base, sugar, or phosphate moieties. Modifications to the base moiety would include natural and synthetic modifications of A, C, G, and T as well as different purine or pyrimidine bases, such as uracil-5-yl, hypoxanthin-9-yl (I), and 2-aminoadenin-9-yl. Base modifications often can be combined with for example a sugar modification, such as 2'-O-methoxyethyl, to achieve unique properties such as increased duplex stability.

Nucleotide analogs can also include modifications of the sugar moiety. Modifications to the sugar moiety would include natural modifications of the ribose and deoxyribose as well as synthetic modifications. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar.

Nucleotide analogs can also be modified at the phosphate moiety. It is understood that these phosphate or modified phosphate linkages between two nucleotides can be through a 3'-5' linkage or a 2'-5' linkage, and the linkage can contain inverted polarity such as 3-5' to 5'-3' or 2'-5' to 5-2'. Various salts, mixed salts and free acid forms are also included. It is understood that nucleotide analogs need only contain a single modification, but may also contain multiple modifications within one of the moieties or between different moieties.

Nucleotide substitutes are nucleotides or nucleotide analogs that have had the phosphate moiety and/or sugar moieties replaced. Nucleotide substitutes include molecules having similar functional properties to nucleotides, but which do not contain a phosphate moiety, such as peptide nucleic acid (PNA). Nucleotide substitutes include molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. It is also understood in a nucleotide substitute that both the sugar and the phosphate moieties of the nucleotide can be replaced, by for example an amide type linkage (aminoethylglycine) (PNA).

DNA molecules of the invention can be made up of different types of nucleotides or the same type of nucleotides. The nucleotides can be comprised of bases (that is, the base portion of the nucleotide) and can comprise different types of bases. For example, one or more of the bases can be universal bases, such as 3-nitropyrrole or 5-nitroindole; about 10% to about 50% of the bases can be universal bases; about 50% or more of the bases can be universal bases; or all of the bases can be universal bases.

One-Step Isothermal Method

One aspect of the invention is an in vitro method, using isolated (e.g., substantially purified) proteins, for joining two or more double-stranded (ds) or single-stranded (ss) DNA molecules of interest, wherein the distal region of the first DNA molecule and the proximal region of the second DNA molecule of each pair share a region of sequence identity, comprising incubating the at least two DNA molecules in a single vessel, at about 45-60° C., with
  (a) a non-thermostable, 5' (51 to 3') exonuclease (e.g., T5 or lambda exonuclease, and/or wherein the exonuclease is not T7 exonuclease),
  (b) a crowding agent (e.g., PEG, such as about 5% PEG, e.g., PEG-8000),
  (c) a thermostable non-strand-displacing DNA polymerase which exhibits a 3' exonuclease activity (e.g., a polymerase that intrinsically exhibits a 3' exonuclease (proofreading) activity, such as PHUSION® or VENT$_R$® DNA polymerase; or a mixture of a polymerase, such as Taq polymerase, which lacks a proofreading activity, and a titered amount (usually a small amount) of an enzyme such as PHUSION® or VENT$_R$® polymerase, which has a 3' exonuclease activity), and
  (d) a thermostable ligase (e.g., Taq ligase),
under conditions that are effective for joining the at least two DNA molecules to form a substantially intact dsDNA molecule (e.g., in which a single copy of the region of sequence identity is retained, and/or in which unpaired, non-homologous, single-stranded DNAs are digested and removed.

In the preferred isothermal method, the polymerase of (c) comprises a 3' exonuclease activity. This enzymatic activity can be an intrinsic property of the polymerase (c); for example, PHUSION® and VENT$_R$® DNA polymerases are thermostable, non-strand-displacing, DNA polymerases which exhibit a proofreading activity (a 3' exonuclease activity). Alternatively, polymerase (c) can be a combination of an enzyme such as Taq polymerase, which lacks a proofreading activity, with a titrated amount (usually a small amount) of a thermostable polymerase such as PHUSION® or VENT$_R$® polymerase, which has a 3' exonuclease activity. This 3' exonuclease activity is useful, for example, when it is desirable to add sequences such as primer binding sites to the ends of the DNA molecules to be joined, e.g., in order to allow PCR amplification of the molecules by universal primers, but then to remove the primer binding sites during the assembly procedure. The ability to use universal primers to amplify DNA molecules to be joined, and then to be able to remove during the assembly reaction the binding domains in the molecules which allow the universal primers to be used, is an advantage of the invention.

An advantage of this method of the invention is that one can join DNA molecules which initially lack 5' phosphorylated ends (e.g., DNAs prepared by PCR amplification), even though a 5' phosphorylated end is required for ligase to join a 5' end to a 3' OH group. This is because the 5' exonuclease, as it removes nucleotides from the 5' end of a substrate DNA, leaves 5' phosphorylated ends.

Without wishing to be bound by any particular theory, it is suggested that, when the mixture of components is incubated at an elevated temperature (about 45-60° C., e.g., at about 50° C.), the DNA polymerase is able to "win" the competition with the exonuclease activity, so that the gaps formed by digestion with the exonuclease are filled in by the polymerase substantially immediately after they are formed. This is achieved because the exonuclease is not thermostable, and thus is weakly active at the elevated temperature and is inactivated after about 10-15 minutes of incubation, whereas the polymerase functions well at the high temperature, driving the reaction to fill in the gaps; the nicked molecules thus formed can then be ligated by the thermostable ligase. By a "thermostable" enzyme is meant an enzyme that can function well at a temperature of at least about 45° C.-60° C.

Because the buffer conditions for assembling DNA molecules by a method of the invention are also suitable for PCR amplification, and an assembly mixture already contains PHUSION® polymerase, PCR can be performed following an assembly reaction without changing the buffer conditions. In one embodiment, once assembly is completed, the vessel holding the reaction components is opened and primers for PCR are added. In another embodiment, the primers are already contained within the assembly mixture from the start of the reaction. In this embodiment, following assembly, the vessel does not have to be opened, and the PCR reaction can begin immediately and proceed by the standard procedure. When primers are contained within the assembly mixture, it may be necessary to add the primers in excess (e.g., ~5,000 nM) of normal primer concentrations in PCR (usually 500 nM), to prevent degradation of some or most of the PCR primers by the exonuclease during the assembly step.

Kits for in vitro joining two or more double-stranded (ds) or single-stranded (ss) DNA by the preferred isothermal method, comprise, in a single container,
  (a) a non-thermostable, 5' exonuclease (e.g., wherein the exo is T5 or lambda exonuclease; wherein the exo is T5; wherein the exo is not T7 exonuclease),
  (b) a crowding agent (e.g., PEG, such as about 5% PEG-8000),
  (c) a thermostable non-strand-displacing DNA polymerase which exhibits a 3' exonuclease activity (e.g., a polymerase that intrinsically exhibits a 3' exonuclease (proofreading) activity, such as PHUSION® and VENT$_R$® DNA polymerase; or a mixture of a polymerase, such as Taq polymerase, which lacks a proofreading activity, and a titered amount (usually a small amount) of an enzyme such as PHUSION® or VENT$_R$® polymerase, which has a 3' exonuclease activity), and
  (d) a thermostable ligase (e.g., Taq ligase),
in suitable amounts such that, when dsDNA molecules or ssDNA oligonucleotides are added to the kit in the presence of a suitable buffer composition and dNTPs and incubated for about 15-60 minutes, at about 45° C. to about 60° C., the DNA molecules are assembled, in a concerted reaction.

In one embodiment, the kit comprises the components of the Oligonucleotide Assembly Mixture shown in Example III A. A kit of the invention may be stored frozen, e.g., at about –20° C.

Any of a variety of 5' to 3', double-strand specific exodeoxyribonucleases may be used to chew-back the ends of DNA molecules in the methods of the invention. The term "5' exonuclease" is sometimes used herein to refer to a 5' to 3' exodeoxyribonuclease. A "non-processive" exonuclease, as used herein, is an exonuclease that degrades a limited number of (e.g., only a few) nucleotides during each DNA binding event. Digestion with a 5' exonuclease produces 3' single-stranded overhangs in the DNA molecules. Among other properties which are desirable for a 5' exonuclease are that it lacks 3' exonuclease activity, it generates 5' phosphate ends, and it initiates degradation from both 5'-phosphorylated and unphosphorylated ends. It also desirable that the enzyme can initiate digestion from the 5' end of a molecule, whether it is a blunt end, or it has a small 5' or 3' recessed end. Suitable exonucleases will be evident to the skilled worker. These include, e.g., phage T5 exonuclease (phage T5 gene D15 product), phage lambda exonuclease, RecE of Rac prophage, exonuclease VIII from *E. coli*, phage T7 exonuclease (phage T7 gene 6 product), or any of a variety of 5' exonuclease that are involved in homologous recombination reactions. In one embodiment of the invention, the exonuclease is T5 exonuclease or lambda exonuclease. In another embodiment, the exonuclease is T5 exonuclease. In another embodiment, the exonuclease is not phage T7 exonuclease. Methods for preparing and using exonucleases and other enzymes employed in methods of the invention are conventional; and many are available from commercial sources, such as USB Corporation, 26111 Miles Road, Cleveland, Ohio 44128, or New England Biolabs, Inc. (NEB), 240 County Road, Ipswich, Mass. 01938-2723.

When a 5' exonuclease is used, single-stranded overhangs are generated at the 5' end of DNA molecules which cannot be repaired, unless, e.g., the molecules can form a circle, or other procedures are introduced to block exonuclease digestion of these 5' termini. Non-strand-displacing DNA polymerases used in methods of the invention must elongate in the 5' direction from a primer molecule. Because no primer is available to be extended in the 5'-located gap in a DNA molecule which has been chewed back with a 5' exonuclease, the gap cannot be filled in by a polymerase. In one embodiment of the invention, the DNA molecules to be joined are selected (designed) so that the two terminal DNA molecules join to one another to form a circle. In another embodiment, the joined DNA molecules are designed so that they become integrated into a vector which is also present in the reaction mixture. Alternatively, in one embodiment of the invention, the 5' ends of the terminal DNA molecules that are to be joined are blocked so that 5' exonuclease cannot digest them. The blocking agent is preferably reversible, so that the joined DNA molecule can eventually be joined into a vector. Suitable blocking agents will be evident to the skilled worker. These include, e.g., phosphorothioate bonds, 5' spacer molecules, locked nucleic acid (LNA), etc.

As is discussed elsewhere herein with regard to the removal of non-homologous sequences, it is desirable that a thermostable, non-strand-displacing, DNA polymerase to be used in a method of the invention exhibits a 3' exonuclease (proofreading) activity. Among suitable DNA polymerases having such a 3' exonuclease activity are PHUSION® polymerase, VENT$_R$® polymerase or DEEP VENT$_R$™ polymerase (which have strand-displacing activity when used at 55° C. or lower), Pfu polymerase and 9° N$_m$™ polymerase. Alternatively, one can use a thermostable, non-strand-displacing, DNA polymerase which lacks a 3' exonuclease activity, if one also includes a small amount of a second enzyme which can provide the 3' exonuclease activity. For example, one can use Taq polymerase, plus a small amount of one of the polymerases noted above that have 3' exonuclease activity. A skilled worker can readily titrate how much of the second enzyme to include, in order to achieve the desired amount of exonuclease activity.

In many of the examples used herein, PHUSION® polymerase is used. This polymerase is desirable because, among other properties, it exhibits a high degree of fidelity.

A kit for conducting this method can comprise (a) an isolated (e.g., substantially purified) enzyme having a non-thermostable, 5' exonuclease activity (e.g., T5 exonuclease or lambda exonuclease, but preferably not T7 exonuclease); (b) a crowding agent, such as PEG (e.g., about 5% final concentration of PEG-8000); (c)(i) an isolated thermostable, non-strand-displacing DNA polymerase which exhibits a proofreading 3' exonuclease activity (e.g., PHUSION® or VENT$_R$® polymerase); or (c)(ii) an isolated thermostable, non-strand-displacing DNA polymerase which does not exhibit a proofreading 3' exonuclease activity (e.g., Taq polymerase), in combination with a suitably small amount of a polymerase having a 3' exonuclease activity (e.g., PHU-SION® or VENT$_R$® polymerase); and (d) an isolated, thermostable ligase (e.g., Taq DNA ligase). Other components of a kit of the invention can include a suitable buffer solution, which comprises a buffer at pH about 7.5 (such as Tris), a suitable amount of MgCl$_2$, the four dNTPs, an energy source (such as ATP or NAD), and, optionally, a suitable cloning (assembly) vector, such as a pUC vector. These components can be packaged in amounts suitable for a single use, in individual vessels, to which DNA molecules to be joined are added; or the components can be present in a larger volume, which can be distributed in aliquots suitable for individual joining reactions.

An exemplary kit contains an optimized 1.33× mixture of Tris pH 7.5, MgGh, the four dNTPs, DTT, PEG-8000, NAD, T5 exonuclease, PHUSION® polymerase, Taq ligase and, optionally, an assembly vector. A kit of the invention is generally packaged in a containers in which the components are stable, e.g., it can be stored frozen, at about −20° C.

In one embodiment of the invention, 5 µL of a pool of dsDNA or ssDNA molecules (e.g., oligonucleotides, such as 60-mers that overlap each other by 20 bases) to be assembled are combined with 15 µL of the mixture of the kit, to generate a total of 20 µL. This mixture is then incubated at about 45-60° C. (e.g., at about 50° C.) for about 15-60 minutes (e.g., 15, 30, 45 or 60 minutes), during which time the DNA molecules assemble into a contiguous segment of dsDNA. If desired, a kit can further contain an assembly vector (e.g., a cloning vector), such as pUC 19, pBR322 or a BAC.

Optionally, kits of the invention comprise instructions for performing the method, e.g., instructions for designing oligonucleotides to be assembled, and/or directions for diluting a pool of oligonucleotides to a suitable concentration. For example, the inventors have found that about 180 fmol/µL of each oligonucleotide in 5 µL is optimal for assembling eight 60-mers with 20 base overlaps. Other optional components of a kit of the invention include a positive control; for the example noted above, a control can contain eight 60-mers with 20 base overlaps that have been demonstrated to assemble by a method of the invention, as well as a vector, such as pUC19. A kit can also contain, if cloning of the assembled DNAs is desired, instructions for transforming the assembled mixture into a suitable microorganism, such as *E. coli*, and selecting for transformants on an agar plate containing growth medium (e.g., LB) and a suitable selective marker (e.g., for pUC19, carbenicillin or ampicillin). A kit can also comprise instructions concerning suitable strains for transformation, parameters for electroporation, etc.

One-Step Thermocycled Method

Another aspect provides a method comprising incubating the ds DNA or ss DNA molecules with
  (a) a non-thermostable, 3' exonuclease operable in the presence of dNTPs, which "chews-back" the ends of the double-stranded DNA molecules, to expose single-stranded overhangs comprising the regions of overlap;
  (b) a crowding agent;
  (c) a thermostable non-strand-displacing DNA polymerase conjugated to a moiety in a temperature-sensitive manner to block the polymerase activity below the activity temperature;
  (d) a thermostable ligase, which seals (ligates) the nicks thus formed;
  (e) dNTPs; and
  (f) a suitable buffer.

The exonuclease of (a) is rendered inactive at a high temperature (e.g., 75° C.). The exonuclease is active at a lower temperature, e.g., 37° C.

The polymerase of (b) may exhibit an activity temperature between 37° C. and 75° C. and the polymerase may be active above this temperature. Without wishing to be bound by a particular mechanism, the inactivating moiety remains conjugated to the polymerase below the activity temperature. At the activity temperature, the antibody becomes unbound and the polymerase exhibits activity. For example, at 75° C., the antibody is unbound from the polymerase and the polymerase is active.

Preferably, the ligase of (c) is thermostable at 75° C. or higher. The ligase need not be active at 75° C. or higher, but if active at a lower temperature, the activity must be present when the temperature is lowered from 75° C. or higher to the lower temperature (e.g., 60° C.).

In the method of the invention, when the mixture of components is first incubated at a low temperature (about 30-45° C., e.g., at about 37° C.), the exonuclease is active and forms gaps on the DNA, while the DNA polymerase is inactive due to steric interference on the part of the bound inhibiting moiety such as an antibody or biotin. When the temperature is raised to a high temperature (above 65° C., e.g., at about 75° C.), the exonuclease is rendered inactive and the DNA polymerase is rendered active as the antibody dissociates from the polymerase. When the temperature is lowered to about 60° C., the ligase is active to fill in the gaps.

The entire procedure is carried out as a "one-step" reaction (in a single tube, which does not have to be opened during the entire recombination procedure, in a thermocycler apparatus). In one such procedure, a mixture of the DNAs to be joined is incubated at 37° C. with exonuclease III; Taq DNA polymerase which is rendered inactive through conjugation to an antibody; Taq DNA ligase; dNTPs and a buffer compatible with all of these enzymatic activities. The temperature is then raised to 75° C. At this temperature, exonuclease III is inactivated, the chewed back DNAs begin to anneal, and the antibody begins to dissociate from Taq DNA Polymerase, resulting in activation. The temperature is then decreased to 60° C. to complete the repair reaction (filling in the gaps and sealing the nicks).

An advantage of a method of the invention is that the particular method allows exonuclease activity in the presence of dNTPs. Without wishing to be bound by a particular mechanism, use of exonuclease III permits exonuclease activity in the presence of dNTPs, while the exonuclease activity of T4 DNA polymerase is blocked by dNTPs. Thus, when using exonuclease III there is no need to stop the reaction and add dNTPs in a separate step.

Another advantage of a method of the invention is that all of the steps may be performed in vitro, as a complete recombination system. Other systems known in the art require transformation into a host cell in order to repair the nucleotide fragments produced. The current system encompasses a repair step in vitro using the ligase such that the transformation into a host cell is avoided. This is particularly useful if the nucleotide to be repaired would be toxic to a host cell and thus not able to undergo transformation.

Yet another advantage of a method of the invention is that the 5' and 3' overhangs are repaired in the nucleotide produced. Other isothermal one-step methods do not involve repairing the 5' and 3' overhangs.

Another aspect of the invention is a kit for the in vitro joining of two or more double-stranded (ds) DNA molecules of interest, wherein the distal region of the first DNA molecule and the proximal region of the second DNA molecule of each pair share a unique region of sequence identity, comprising, in a single container, (a) a non-thermostable, 3' (3' to 5') exonuclease operable in the presence of dNTPs,
(b) a crowding agent,
(c) a thermostable non-strand-displacing DNA polymerase conjugated to a chemical moiety in a temperature sensitive manner to block the polymerase activity below the activity temperature, and
(d) a thermostable ligase, and optionally
(e) dNTPs, and
(f) a suitable buffer, in suitable amounts such that, when dsDNA molecules or ssDNA oligonucleotides and when needed, dNTPs, a crowding agent, and as suitable buffer, are added to the contents of the mixture and incubated for about two to ten minutes, at 37° C., then 10-40 minutes at 75° C., and then for 30 minutes to two hours at 60° C., the DNA molecules are assembled. A kit of the invention may be stored frozen, e.g., at about −20° C.

In an embodiment of this aspect, in step (c) the incubation steps may be five minutes at 37° C., then 20 minutes at 75° C., and then for one hour at 60° C.

Any of a variety of 3'→5', double-strand specific exodeoxyribonucleases may be used to chew-back the ends of DNA molecules in the methods of the invention. The term "3' exonuclease" refers to a 3'→5' exodeoxyribonuclease. Suitable exonucleases will be evident to the skilled worker. These include, e.g., exonuclease III. In one embodiment of the invention, the exonuclease is exonuclease III. Methods for preparing and using exonucleases and other enzymes employed in methods of the invention are conventional; and many are available from commercial sources, such as USB Corporation, 26111 Miles Road, Cleveland, Ohio 44128, or New England Biolabs, Inc. (NEB), 240 County Road, Ipswich, Mass. 01938-2723.

Preferably in the one-step thermocycled method, the 3' exonuclease is not active as a polymerase.

Combinatorial Methods for Optimization

In preferred embodiments, the isothermal methods of the present invention can be used to modify the properties of a whole nucleic acid molecule, for example, to optimize the expression, function, activity, yield, etc., of a polypeptide encoded by the nucleic acid molecule. The combinatorial methods described herein provide a multitude of possible nucleic acid sequences that can be screened for the desired outcome. In alternative embodiments, the nucleic acids could provide other DNA or RNA products, for example, antisense RNA that is used to decrease the yield of another product in a host cell. The outcome of the combinatorial approach is to provide a desired product that is not found in nature, or is an improvement or optimization of a natural product. Optimized products may be synthetic components, natural components that have been modified or rearranged, or combinations of natural and synthetic components. One of skill in the art could envision multiple additional applications of the combinatorial methods described herein.

Whatever the level at which recombination occurs, the intermediate product is a mixture of nucleic acids encoding proteins that typically are expressed and tested for yield and, in the embodiments other than codon optimization, activity. Thus, typically the mixture of nucleic acids is provided with restriction sites or overlapping portions that permit insertion of the nucleic acids into expression systems that contain control sequences, notably promoters and termination signals. The choice of control sequences, depends, of course, on the host in which expression is to take place. The optimal control sequences for any particular intended host can also be determined by constructing appropriate libraries containing a multiplicity of control sequences such as promoters, enhancers and termination sequences and assembled in a multiplicity of genes wherein the most favorable assembly of control sequences can be identified. Convenient hosts include *E. coli*, other bacterial systems and yeast as well as other unicellular fungi. Mammalian host cells or insect host cells could also be used as could plant cells. The choice of the host for testing is a matter of experimental preference and expression controls for all of these hosts are well known.

Once the mixture has been treated to insert the coding sequences into expression systems, it is used to transfect the appropriate cells which are then diluted and cultured. Depending on the desired end point, the protein activity, yield or metabolic activity of the cultures is assessed for the culture with the highest value. The nucleic acid is then retrieved from this culture and sequenced or otherwise identified as the desirable sequence or sequences. Depending on the level of optimization—i.e., codon usage, individual protein optimization, metabolic pathway optimization, or gene synthesis, the next combinatorial step can be achieved by assembling optimal components.

Methods of in vitro assembly described above may be used to conduct this process. Additionally, methods of in vivo assembly may be used to conduct this process, as described above. Furthermore, a combination of in vitro and in vivo assembly may be used to conduct this process.

However, as to the various recombination systems, the initial steps of nucleic acid construction differ in their components.

Figure 7A:
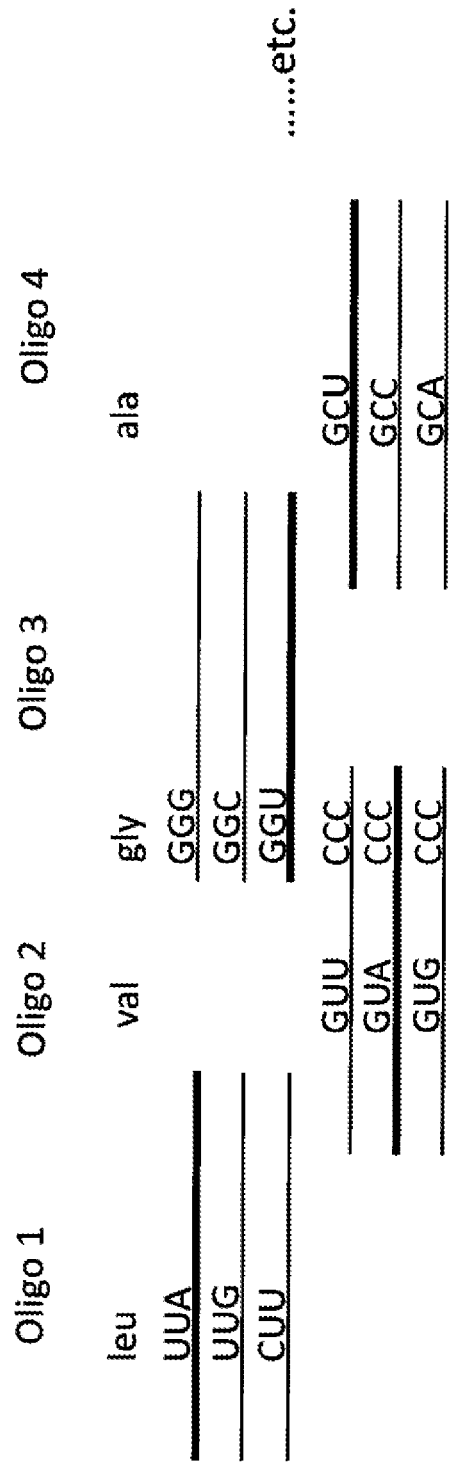
FIG. 7A is a schematic illustrating the use of codon optimization to create a combinatorial library of assembled fragments.

For codon optimization, as shown in FIG. 7A, a coding sequence is constructed as shown therein by varying the codons in each nucleic acid used to assemble the coding sequence. As shown in FIG. 7A, a protein that includes leucine, valine, glycine and alanine is assembled from individual fragments where the codons for these individual amino acids is varied. By suitable overlap segments, a mixture containing all of the nucleotides shown in FIG. 7A can be assembled in the correct order in a single reaction mixture as described above. The resultant will be full-length coding sequences. If desired, an expression vector may also be added to the mixture to provide the control sequences automatically at this stage. The assembled coding sequences provided further with expression controls, if necessary, are then transfected into host cells, and cultured individually and the level of protein assessed using standard protein determination techniques. The colonies with the highest levels of protein production are analyzed by extracting the expression system and sequencing to identify the optimal set of codons.

In general, while highest levels of production or activity are referred to, it is understood that it is not necessary to select the exact highest value in each case. For various reasons, it may be sufficient simply to select for satisfactory levels of these characteristics.

In more detail, a method to identify a nucleotide sequence that optimizes codon usages for production of a protein comprises at least the following steps (a) through (e). In step (a), oligomers are provided encoding portions of the protein containing degenerate forms of the codon for an amino acid encoded in the portions, with the oligomers extended to provide flanking coding sequences with overlapping sequences. In step (b), the oligomers are treated to effect assembly of the coding sequence for the protein. The reassembled protein is included in an expression system that is operably linked to control sequences to effect its expression. In step (c), the expression system is transfected into a culture of compatible host cells. In step (d), the colonies obtained from the transformed host cells are tested for levels of production of the protein. In step (e), at least one colony with the highest or a satisfactory production of the protein is obtained from the expression system. The sequence of the portion of the expression system that encodes the protein is determined.

For an embodiment wherein control sequences are to be optimized, one or more coding sequences are used in the construction of a library containing a multiplicity of expression systems. The components to be assembled into the expression systems include a variety of promoters, enhancers, termination sequences and the like, the selection of which will depend on the nature of the intended recombinant host. Again, the components are provided with overlapping sequences to assure assembly in the correct order. Using any in vitro assembly technique, a variety of genes with different control sequences is obtained which are then transfected into host cells and cultured individually to determine levels of protein production.

In more detail, to construct a gene with optimal control sequences for expression, the method comprises at least the following steps (a) through (e). In step (a), oligomers representing a multiplicity of promoters, enhancers, and termination sequences and oligomers comprising encoding sequences for a protein are provided. In step (b), oligomers to affect assembly of genes for the protein are treated. In step (c), the resulting genes are transfected into a culture of compatible host cells. In step (d), colonies obtained from the transformed host cells are tested for levels of production of the protein. In step (e), the gene is obtained from at least the colony with the highest or satisfactory level of production of the protein. The sequence of the control sequences associated with the nucleotide sequence encoding the protein is determined.

Figure 7B:
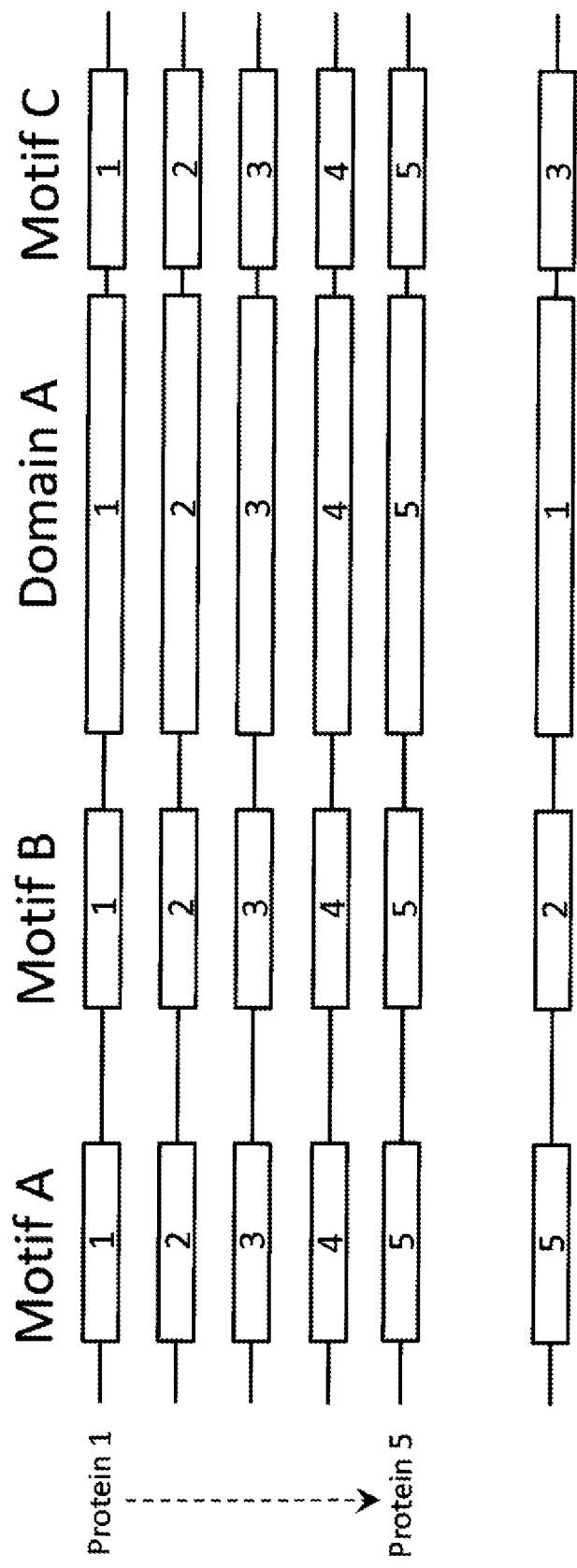
FIG. 7B is a schematic illustrating the use of a multiplicity of motif and domain variants to create a combinatorial library of a gene.

At the next level, illustrated in FIG. 7B, the coding sequences of several variants of a protein of given activity are assessed for motifs and domains. Nucleic acid sequences encoding each of the motifs and domains shown are then individually synthesized and provided suitable overlapping sequences to provide a correct order of assembly. These synthetic sequences are then provided in a ligation mixture similar to that described above with respect to codon optimization, optionally including a vector to provide control sequences, and the resulting expression systems are transfected into host cells and tested for activity and/or yield.

To identify a nucleotide sequence that encodes an optimized form of a protein having a desired activity, the method comprises the following steps (a) through (f). In step (a), domains and motifs contained in a series of variants of the protein are identified. In step (b), oligomers encoding each of the domains and motifs from the variants are provided. In step (c), the mixture is treated to effect assembly into sequences encoding the protein. The assembly is conducted so as to provide the coding sequences with operably linked control sequences for expression, to obtain a mixture of expression systems. In step (d), the expression systems are transformed into a culture of compatible host cells. In step (e), the colonies obtained from the cells are tested for activity of the produced protein. In step (f), the expression system is isolated from at least the colony that produces the protein of highest or satisfactory level of activity. The nucleotide sequence encoding said protein is then identified.

Figure 7C:
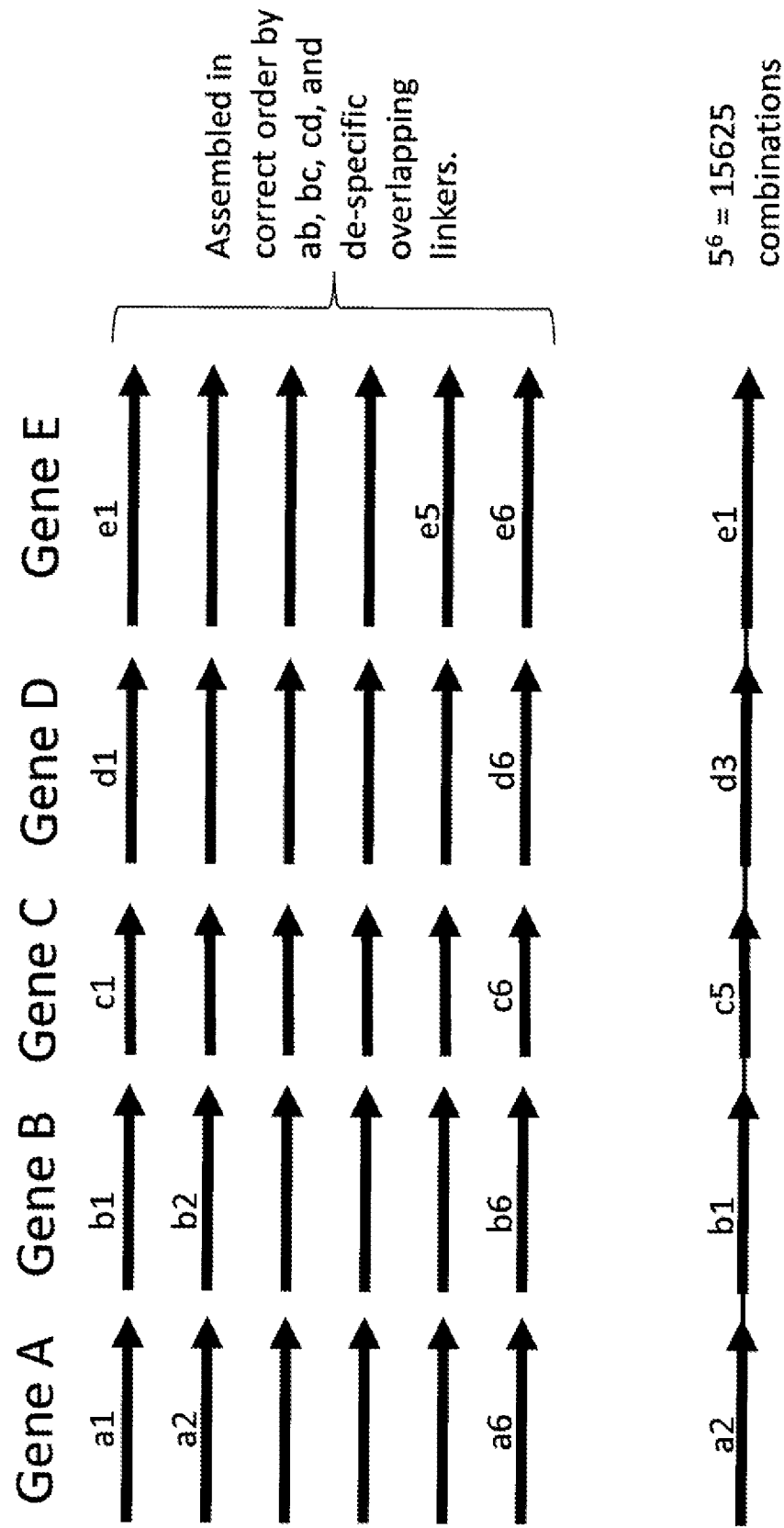
FIG. 7C is a schematic illustrating the use of variant genes to create a combinatorial library of a metabolic pathway.
Figure 8A:
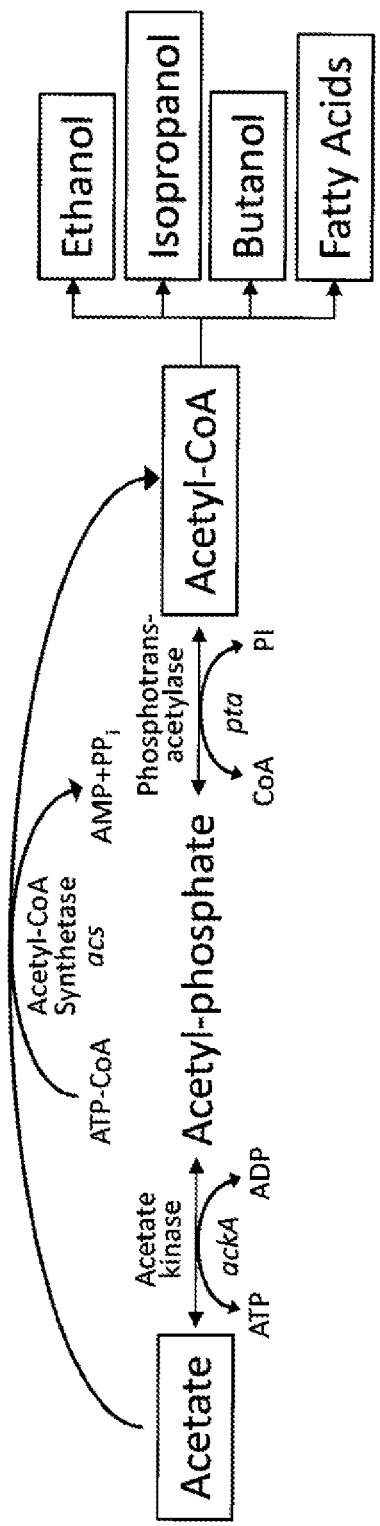
FIG. 8A is a schematic of an acetate utilization pathway.
Figure 8B:
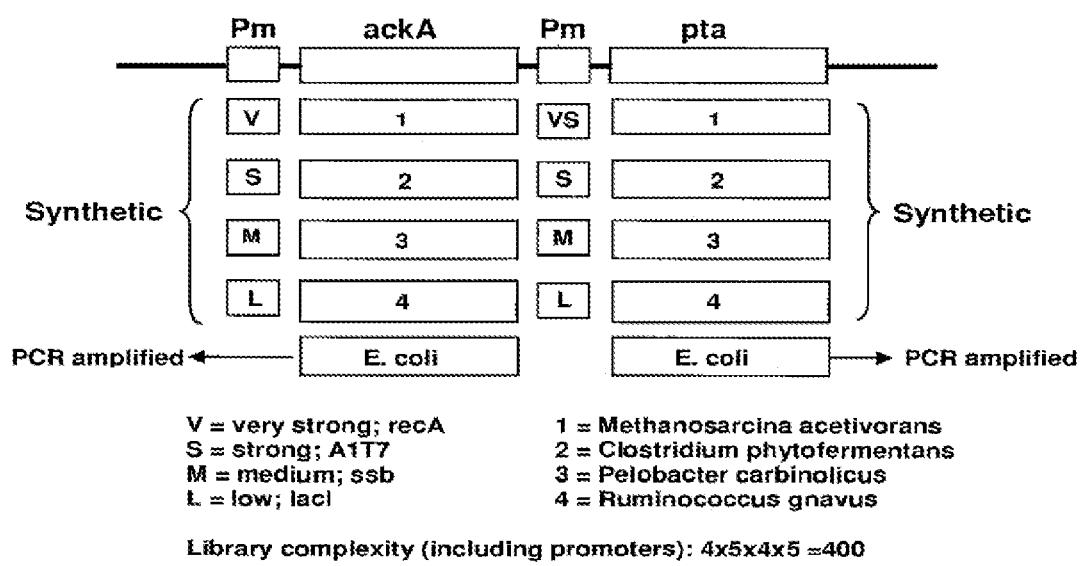
FIG. 8B is a schematic illustrating the use of variant genes from 5 organisms together with 4 control sequences to create a combinatorial library of the acetate utilization pathway shown in FIG. 8A.
Figure 8C:
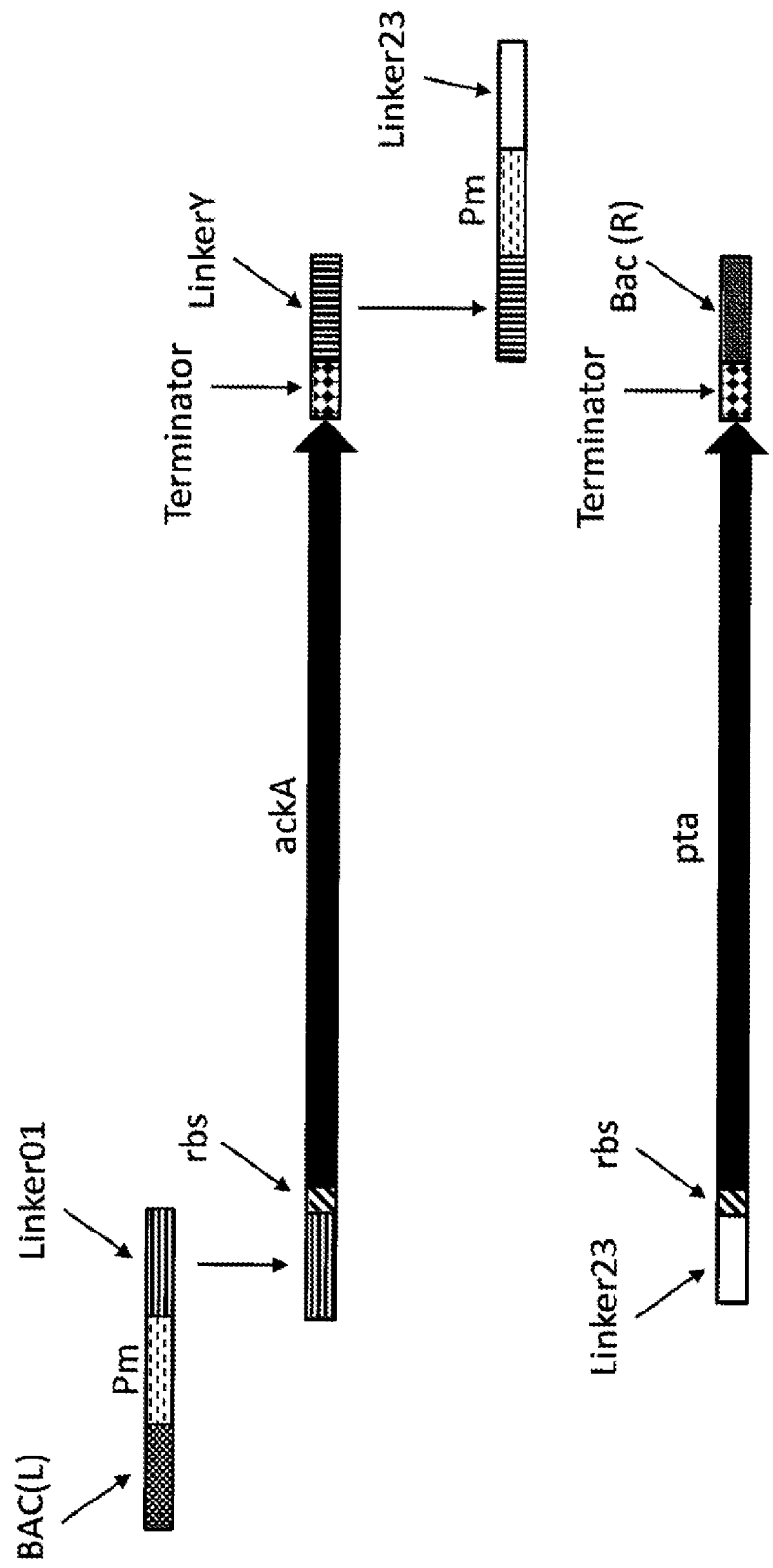
FIG. 8C is a schematic illustrating the assembly strategy for the nucleic acid fragments shown in FIG. 8B.
Figure 8D:
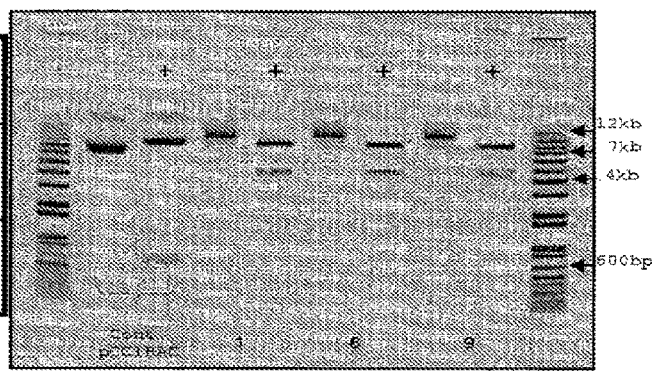
FIG. 8D shows the results of the assembly of an exemplary acetate utilization pathway as shown in FIG. 8C, showing assembly product released from the vector by restriction enzyme digest.
Figure 9A:
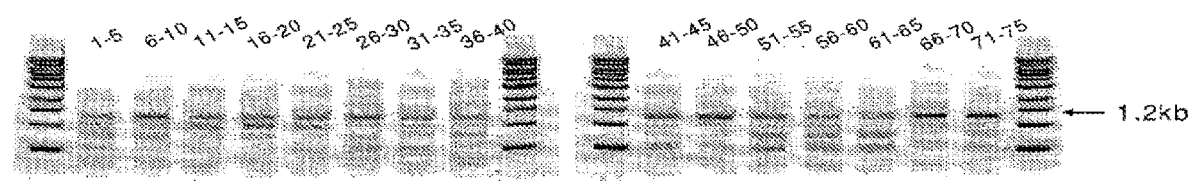
FIG. 9A-9F show the sequential assembly of a complete mouse mitochondrial genome using the method shown in FIG. 5A (T5 exonuclease).
Figure 9B:
Figure 9C:
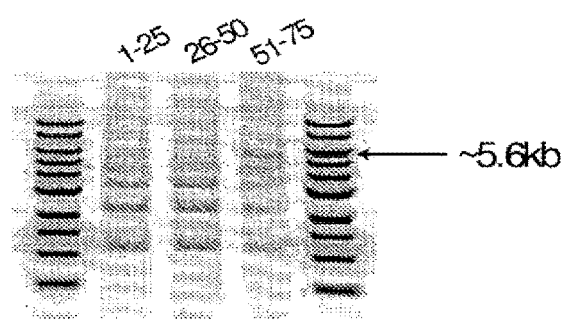
Figure 9D:
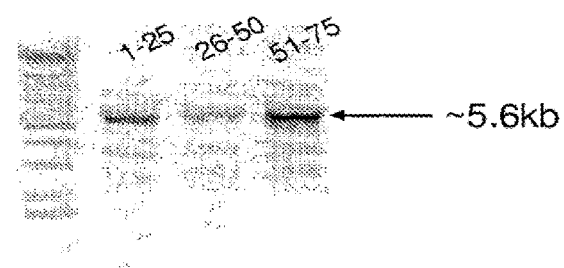
Figure 9E:
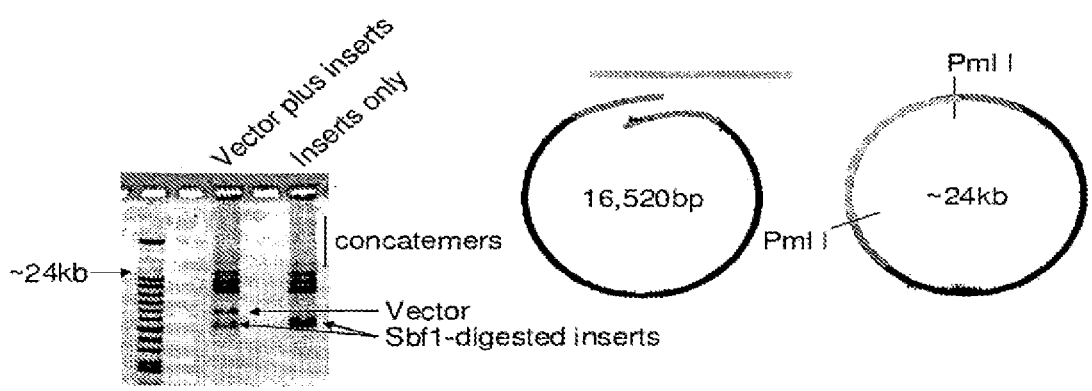
Figure 9F:
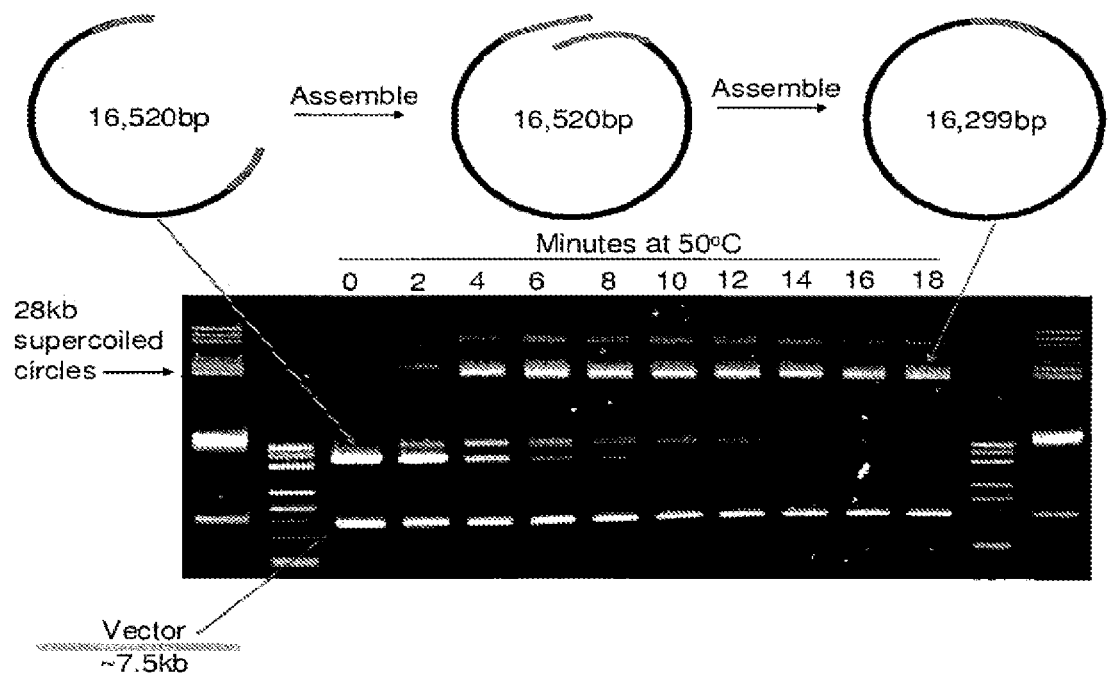

At the next level, shown in FIG. 7C, variants of proteins that are responsible for a metabolic pathway are individually synthesized, mixed and matched as described above, and tested for the production of metabolic products. The pathways may be assembled on a single vector or multiple vectors may be used in successive transformations. Variants may include upstream promoter elements of the genes encoding the proteins from different species as well as synthetically generated upstream promoter elements.

Finally, in one embodiment, assemblies of the desirable metabolic pathways and/or genes may be combinatorially assembled into complete genomes using a similar approach. As described in Gibson, et al., *Science* (2008) 319:1215-1220, an entire bacterial genome can be assembled by a combination of in vitro and in vivo techniques. Minimal genomes may also be assembled in this way.

In one embodiment, entire pathways may be assembled using appropriate linkers to construct an entire genome. The methods for assembly and testing are similar to those described above. Because assembly of several DNA pieces takes place in a single reaction operating at a single temperature, it is possible to carry out the reaction in a highly parallel fashion to build, in stages, an entire chromosome. The pathway variants may all be cloned into a bacterial artificial chromosome (BAC) vector, or any other vector useful for the manipulation of large nucleic acids.

To optimize metabolic pathways, the method comprises constructing nucleic acid molecules encoding variants of each enzyme in the pathway to be optimized. All of the encoding sequences can be assembled using the technique described above of overlapping sequences on a single vector for each different pathway, or independent vectors for each member of the pathway can be employed by mixing the vectors for each member in successive transformation mixtures. Control sequences to effect expression of the enzymes in the pathway are provided. Colonies derived from the culture are assessed for favorable characteristics conferred by the pathway to be optimized, and the expression systems of successful colonies are sequenced.

The construction of optimal or minimal genomes need not be based solely on a combination of metabolic pathway assemblies. Individual genes may also be assembled in a similar manner or a combination of individual genes and metabolic pathways may be so assembled. To determine the necessity for one or more genes to a metabolic pathway, each of these could be systematically eliminated from the assembly.

In all of the foregoing methods, DNA molecules can be assembled using robotic systems at some or all of the levels described. At any stage, either in vitro or in vivo methods may be used. Assembly of entire genomes may be desirable. Using the techniques described by Gibson, et al., chromosomes of 20-500 kb can be constructed in a combinatorial manner as described above. For assembly of nucleotide sequences that generate complete optimized metabolic pathways the optimal combination of these systems is evaluated.

The processes described above may be conducted ab initio, without preselection of putatively desirable elements or may include selection of appropriate variant genes for each of the pathway genes from sequence databases, from all available sequence libraries including completed genomes and environmental libraries. Computational approaches may be used to select the most likely candidates from the many available choices. Results with one combinatorial library might help to design a second library for the same pathway that would give even better production of the desired product.

Optimum codon usage for expression in the chosen production host cell can also be designed based on computational methods and tested as described above.

As noted above, appropriate regulatory signals are added for the chosen production host, including transcriptional promoters and terminators, and appropriate signals for initiation of protein synthesis, as well as suitable linker sequences specific for each gene-gene junction in the pathway and for joining the assembled pathway to the cloning vector.

Optimal sizes and overlaps of the individual oligonucleotides for the entire assembly, may also be designed. Design tools include a graphical interface to aid in initial pathway design and to view the final sequence design. In the case of combinatorial libraries it should be possible to call up and view any individual chromosome within the library with a single mouse click on each component gene.

As to assembly of a pathway, for illustration, assuming an average gene size of 1200 bp and an average oligonucleotide size of 60 nucleotides, roughly $1200 \times 9 \times 10 \times 2/60 = 3,600$ oligonucleotides are needed for the construction of a 9 gene pathway, excluding control elements which are small relative to genes. The factor of 2 is because the oligonucleotides have to cover both strands of the DNA. Oligonucleotides can be purchased from any of a dozen or so suppliers, or synthesized automatically. The oligonucleotides, which are supplied in 96-well oligonucleotide trays, are robotically distributed into 96-well assembly reaction trays such that each well in the assembly trays would contain 8 adjacent oligonucleotides in the sequence. The number of trays could then be reduced at the first assembly step from approximately 36 oligonucleotide trays down to around 5 assembly trays. A 15 µl aliquot of the thawed assembly reaction mixture (which already includes the cloning vector as a ninth DNA piece) is transferred to each well. The trays are then incubated for 20 minutes at 50° C. The assembly product in each well consists of 8 assembled oligonucleotides inserted into the vector DNA to form a circle. Aliquots of each well are pooled together, cloned and sequenced. Correct clones are transferred back into 5 trays for the next assembly step. By sequencing up front at the first stage of assembly when the assemblies are small, oligonucleotide errors are weeded out, and all subsequent assemblies will generally have correct sequence.

To go from one assembly step to the next, the assemblies are "lifted out" of the vector by high fidelity PCR and aliquots are distributed to the next set of trays for the next assembly reaction.

Assembly continues until a single tray contains 10 variants of each of the 9 genes. The 9 genes and their variants are then pooled into a final assembly reaction that results in a library of 10$^9$ different combinations of the 9 gene pathway cloned into the BAC vector. This combinatorial library is transformed into the appropriate host cell, and individual clones are screened for product yield, etc.

The invention thus provides a method of assembling entire genomes by using the optimized components described above. As noted above, the "entire" genome may be a minimal genome, the nature of which is determinable as described in the above-cited PCT publication or may be determined arbitrarily by selecting only certain identified components of the library desired. The library components may be individual genes, assemblies of individual genes according to metabolic pathways, assemblies of genes that are otherwise organized, or a combination of individual genes and organized systems thereof. Desirably, the components are indeed optimized as described herein; however, this is not a prerequisite. Libraries of individual genes and/or assemblies of genes, some or all of which may be optimized with regard to motif variants, control sequences and/or codon usage may be used in the genome assembly.

EXAMPLES

In the following examples, all temperatures are set forth in uncorrected degrees Celsius; and, unless otherwise indicated, all parts and percentages are by weight.

What is claimed is:

1. An in vitro method of joining a set of two or more double-stranded (ds) or single-stranded (ss) DNA molecules, wherein adjacent DNA molecules to be joined contain overlapping sequences at their termini, said method comprising contacting in vitro the two or more DNA molecules in a single vessel with a mixture of components comprising:

(a) an isolated 5' to 3' exonuclease;

(b) an isolated DNA polymerase, (c) an isolated ligase, (d) a mixture of dNTPs, and (e) a suitable buffer, under isothermal conditions at a temperature of 45-60° C. and in amounts effective for joining the two or more DNA molecules to form a first assembled dsDNA molecule in a concerted reaction in said single vessel.

2. The method of claim 1, wherein the exonuclease of (a) is a T5 exonuclease.

3. The method of claim 1, further comprising a crowding agent.

4. The method of claim 3, wherein the crowding agent is selected from PEG and/or dextran.

5. The method of claim 3, wherein the crowding agent is PEG.

6. The method of claim 2, wherein the ligase of (c) is Taq ligase.

7. The method of claim 1, wherein the ligase of (c) is Taq ligase.

8. The method of claim 1, wherein the conditions are also suitable for digesting any unpaired, non-homologous, single-stranded DNAs following the joining reaction.

9. The method of claim 8, wherein at least some of the DNA molecules to be joined comprise, at one terminus, a sequence that is non-homologous to any of the DNA molecules of interest, and wherein the non-homologous sequences comprise one or more binding regions for PCR primers, and/or regions of homology to vector sequences, and/or recognition sites for one or more restriction enzymes.

10. The method of claim 1, further comprising repeating the method to join a second set of two or more DNA molecules to one another to obtain a second assembled DNA molecule, and then joining the first and the second assembled DNA molecules to obtain a third assembled ds DNA molecule.

11. The method of claim 1, wherein the DNA polymerase has 3' exonuclease activity.

12. The method of claim 1, wherein the DNA polymerase and the ligase are thermostable.

13. The method of claim 1, wherein the isothermal conditions occur at a temperature of 50° C.

14. The method of claim 3, wherein the 5' to 3' exonuclease lacks 3' exonuclease activity.

15. The method of claim 14, wherein the exonuclease of (a) is a T5 exonuclease.

16. The method of claim 15, wherein the crowding agent is selected from PEG and/or dextran.

17. The method of claim 16, wherein the crowding agent is PEG.

* * * * *

```
                        SEQUENCE LISTING

<160> NUMBER OF SEQ ID NOS: 16

<210> SEQ ID NO 1
<211> LENGTH: 40
<212> TYPE: DNA
<213> ORGANISM: Artificial sequence
<220> FEATURE:
<223> OTHER INFORMATION: Forward primer for F1 Fragment of Clostridium
      cellulolyticum genomic DNA

<400> SEQUENCE: 1
gcagcttcaa gtcctgcaaa caaggtgtac caggatcgtt                          40

<210> SEQ ID NO 2
<211> LENGTH: 40
<212> TYPE: DNA
<213> ORGANISM: Artificial sequence
<220> FEATURE:
<223> OTHER INFORMATION: Reverse primer for F1 Fragment of Clostridium
      cellulolyticum genomic DNA

<400> SEQUENCE: 2
gatttcagtg tagttagggc cagttgaatt caaacctgcc                          40

<210> SEQ ID NO 3
<211> LENGTH: 40
<212> TYPE: DNA
<213> ORGANISM: Artificial sequence
<220> FEATURE:
<223> OTHER INFORMATION: Forward primer for F2 Fragment of Clostridium
      cellulolyticum genomic DNA

<400> SEQUENCE: 3
ggcaggtttg aattcaactg gccctaacta cactgaaatc                          40

<210> SEQ ID NO 4
<211> LENGTH: 40
<212> TYPE: DNA
<213> ORGANISM: Artificial sequence
<220> FEATURE:
<223> OTHER INFORMATION: Reverse primer for F2 Fragment of Clostridium
      cellulolyticum genomic DNA

<400> SEQUENCE: 4
cttggtgcca tcagcattgt tctctgtacc gcccactgtc                          40

<210> SEQ ID NO 5
<211> LENGTH: 40
<212> TYPE: DNA
<213> ORGANISM: Artificial sequence
<220> FEATURE:
<223> OTHER INFORMATION: Forward primer for F3 Fragment of Clostridium
      cellulolyticum genomic DNA

<400> SEQUENCE: 5
gacagtgggc ggtacagaga acaatgctga tggcaccaag                          40

<210> SEQ ID NO 6
<211> LENGTH: 40
<212> TYPE: DNA
<213> ORGANISM: Artificial sequence
```

-continued

<220> FEATURE:
<223> OTHER INFORMATION: Reverse primer for F3 Fragment of Clostridium
      cellulolyticum genomic DNA

<400> SEQUENCE: 6
cagttgaata atcatgtgtt cctgcggcaa atgcagtacc                           40

<210> SEQ ID NO 7
<211> LENGTH: 40
<212> TYPE: DNA
<213> ORGANISM: Artificial sequence
<220> FEATURE:
<223> OTHER INFORMATION: Forward primer for F4 Fragment of Clostridium
      cellulolyticum genomic DNA

<400> SEQUENCE: 7
ggtactgcat ttgccgcagg aacacatgat tattcaactg                           40

<210> SEQ ID NO 8
<211> LENGTH: 40
<212> TYPE: DNA
<213> ORGANISM: Artificial sequence
<220> FEATURE:
<223> OTHER INFORMATION: Reverse primer for F4 Fragment of Clostridium
      cellulolyticum genomic DNA

<400> SEQUENCE: 8
ttatttacca agaacctttg cctttaacat tgcaaagtca                           40

<210> SEQ ID NO 9
<211> LENGTH: 39
<212> TYPE: DNA
<213> ORGANISM: Artificial sequence
<220> FEATURE:
<223> OTHER INFORMATION: Forward primer for F5 Fragment of Mycoplasma
      gallisepticum genomic DNA

<400> SEQUENCE: 9
gcttgcatgc atcctgttta ttcatcacaa acattgaac                            39

<210> SEQ ID NO 10
<211> LENGTH: 47
<212> TYPE: DNA
<213> ORGANISM: Artificial sequence
<220> FEATURE:
<223> OTHER INFORMATION: Reverse primer for F5 Fragment of Mycoplasma
      gallisepticum genomic DNA

<400> SEQUENCE: 10
aattctgcag ttttttatttc ctaacagaac atttttttcta gtatagc                 47

<210> SEQ ID NO 11
<211> LENGTH: 39
<212> TYPE: DNA
<213> ORGANISM: Artificial seqeunce
<220> FEATURE:
<223> OTHER INFORMATION: Forward primer for F7 Fragment of Mycoplasma
      gallisepticum genomic DNA

<400> SEQUENCE: 11
cgactctaga taaatagcct ttctttatct ttttgaggc                            39

<210> SEQ ID NO 12
<211> LENGTH: 39
<212> TYPE: DNA
<213> ORGANISM: Artificial sequence
<220> FEATURE:

-continued

```
<223> OTHER INFORMATION: Reverse primer for F7 Fragment of Mycoplasma
      gallisepticum genomic DNA

<400> SEQUENCE: 12
ccggggatcc ctttctcaat tgtctgctcc atatatgtt                             39

<210> SEQ ID NO 13
<211> LENGTH: 62
<212> TYPE: DNA
<213> ORGANISM: Artificial sequence
<220> FEATURE:
<223> OTHER INFORMATION: Forward primer for F6 Fragment of pRST21

<400> SEQUENCE: 13
tagaaaaaat gttctgttag gaaataaaaa ctgcagaatt aaaagttagt gaacaagaaa     60
ac                                                                     62

<210> SEQ ID NO 14
<211> LENGTH: 56
<212> TYPE: DNA
<213> ORGANISM: Artificial sequence
<220> FEATURE:
<223> OTHER INFORMATION: Reverse primer for F6 Fragment of pRST21

<400> SEQUENCE: 14
agcctcaaaa agataaagaa aggctattta tctagagtcg acctgcagtt cagatc         56

<210> SEQ ID NO 15
<211> LENGTH: 55
<212> TYPE: DNA
<213> ORGANISM: Artificial sequence
<220> FEATURE:
<223> OTHER INFORMATION: Forward primer for F8 Fragment of pRST21

<400> SEQUENCE: 15
tgttcaatgt ttgtgatgaa taaacaggat gcatgcaagc ttttgttccc tttag          55

<210> SEQ ID NO 16
<211> LENGTH: 51
<212> TYPE: DNA
<213> ORGANISM: Artificial sequence
<220> FEATURE:
<223> OTHER INFORMATION: Reverse primer for F8 Fragment of pRST21

<400> SEQUENCE: 16
aaacatatat ggagcagaca attgagaaag ggatccccgg gtaccgagct c               51
```